US007238861B2

(12) United States Patent
Kasukabe et al.

(10) Patent No.: US 7,238,861 B2
(45) Date of Patent: Jul. 3, 2007

(54) PLANT HAVING IMPROVED TOLERANCE TO VARIOUS ENVIRONMENTAL STRESSES, METHOD OF CONSTRUCTING THE SAME AND POLYAMINE METABOLISM-RELATING ENZYME GENE

(75) Inventors: Yoshihisa Kasukabe, Otsu (JP); Izumi Ihara, Otsu (JP); Shoji Tachibana, Age-gun (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 494 days.

(21) Appl. No.: 10/380,913

(22) PCT Filed: Aug. 31, 2001

(86) PCT No.: PCT/JP01/07521

§ 371 (c)(1),
(2), (4) Date: Mar. 20, 2003

(87) PCT Pub. No.: WO02/23974

PCT Pub. Date: Mar. 28, 2002

(65) Prior Publication Data

US 2003/0163851 A1 Aug. 28, 2003

(30) Foreign Application Priority Data

Sep. 20, 2000 (JP) ............................. 2000-285423
Feb. 8, 2001 (JP) ............................. 2001-032627

(51) Int. Cl.
*C12N 15/82* (2006.01)
*C12N 15/87* (2006.01)
*C12N 5/14* (2006.01)
*C07H 21/00* (2006.01)
*A01H 5/00* (2006.01)

(52) U.S. Cl. .................. 800/289; 435/320.1; 435/468; 435/419; 530/370; 536/23.6; 800/290

(58) Field of Classification Search ..................... None
See application file for complete search history.

(56) References Cited

FOREIGN PATENT DOCUMENTS

| JP | 2000-290102 A | 10/2000 |
|---|---|---|
| JP | 2002-290102 | 10/2000 |
| JP | 2001-046079 | 2/2001 |
| WO | WO 00/67558 | 11/2000 |
| WO | WO 01/09358 A1 | 2/2001 |
| WO | WO 01/11062 A2 | 2/2001 |

OTHER PUBLICATIONS

Keskin et al. (Protein Science, 13:1043-1055, 2004).*
Thornton et al. (Nature structural Biology, structural genomics supplement, Nov. 2000).*
Guo et al. (PNAS, 101: 9205-9210, 2004).*
Hashimoto et al. (Plant Cell Physiol., 39:73-79, 1998).*
Valvekens et al. (PNAS, 85:5536-5540, 1988).*
Bouchereau et al. (Plant Science, 140:103-125,1999).*
Yoder et al. (Bio/Technology, 12:263-267, 1994).*
Roy, M., et al., "Arginine decarboxylase transgene expression and analysis of environmental stress tolerance in transgenic rice", Plant Sci., vol. 160, No. 5, p. 869-875, Apr. 2001.
Minocha, S.C., et al., "Stress tolerance in plants through transgenic manipulation of polyamine biosynthesis", Plant Physiol., vol. 114, No. 3, suppl., p. 297, 1997.
Masgrau, C., et., "Inducible overexpression of oat arginine decarboxylase in transgenic tobacco plants", Plant J., vol. 11., No. 3, p. 465-473, 1997.
Burtin, D., et al., "Overexpression of arginine decarboxylase in transgenic plants", Biochem J., vol. 325, part 2, p. 331-337, 1997.
Noury, M., et al., "A transgenic rice cell lineage expressing the oat arginine decarboxylase (adc) cDNA constitutively accumulates putrescine in callus and seeds but no in vegetative tissue", Plant Mol. Biol., vol. 43, No. 4., p. 537-544, Jul. 2000.
Hashimoto, T., et al., "Molecular cloning of plant spermidine synthases", Plant Cell Physiol., vol. 39, No. 1, p. 73-79, 1998.
Mad Arif, S. A., et al., "Characterization of the S-adenosylmethionine decarboxylase (SAMDC) gene of potato", Plant Mo. Biol., vol. 26, No. 1, p. 327-338, 1994.
Bolle, C., et al., "A spinach cDNA with homology to S-Adenosylmethionine decarboxylase", Plant Physiol., vol. 107, No. 4, p. 1461-1462, 1995.
Perez-Amador, M.A., et al., "Expression of arginine decarboxylase is induced during early fruit development and in young tissues of *Pisum sativum* (L.)", Plant Mol. Biol., vol. 28, No. 6, p. 997-1009, 1995.
Rastogi, R., et al., "Cloning of tomato (*Lycopersicon esculentum* Mill.) arginine decarboxylase gene and its expression during fruit ripening", Plant Physiol., vol. 103, No. 3, p. 829-834, 1993.
Shen, W., et al., "Oxygen Radical Generation in Chilled Leaves of Cucumber (*Cucumis sativus* L.) Cultivars with Different Tolerances to Chilling Termperatures", J. Japan Soc. Hortic. Sci., vol. 68,, No. 4, p. 780-787, Jul. 1999.
Shen, W., et al., "Effect of Cold Treatment on Enzymic and Nonenzymic Antioxidant Activities in Leaves of Chilling Tolerant and Chilling-Sensitive Cucumber (*Cucumis sativus* L.) Cultivars", J. Japan Soc. Hortic. Sci., vol. 68, No. 5, p. 967-973, Sep. 1999.
Shen W., et al. "Involvement of Polyamines in the Chilling Tolerance of Cucumber Cultivars", Plant Physiol., vol. 124, p. 431-439, 2000.

(Continued)

*Primary Examiner*—Ashwin Mehta
*Assistant Examiner*—Vinod Kumar
(74) *Attorney, Agent, or Firm*—Kenyon & Kenyon LLP

(57) ABSTRACT

The present invention relates to isolated plant-derived polyamine metabolism-related enzyme genes characterized in that their level of expression changes when exposed to environmental stress; antisense DNA or antisense RNA to such genes; plants and their progeny having improved environmental stress tolerance, in which such genes are retained in a stable manner; methods for producing such plants, and methods for producing calli of such plants; method for selecting transformed plants which grow improved more than plants lacking an exogenous polyamine metabolism-related enzyme gene; and microorganims and plants which are transformed by such genes

11 Claims, 13 Drawing Sheets

OTHER PUBLICATIONS

Krishnamurthy, R., et al., "Polyamines as Modulators of Salt Tolerance in Rice Cultivars", Plant Physiol., vol. 91, p. 500-504, 1989.

Nam, Kyoung, Hee, et al., "Differential Expression of ADC mRNA during Development and upon Acid Stress in Soybean (*Glycine max*) Hypocotyls", Plant Cell Physiol., 38 (10), p. 1156-1166, 1997.

Flores, H.E., et al., "Osmotic Stress-Induced Polyamine Accumulation in Cereal Leaves", Plant Physiol., vol. 75, p. 102-109, 1984.

Torrigiani, P., et al., "Polyamine synthesis and accumulation in the hypersensitive response to TMV in *Nicotiana tabacum*", New Phytol., 135, p. 467-473, 1997.

Kurepa, J., "Polyamines and Paraquat Toxicity in *Arabidopsis thaliana*", Plant Cell Physiol., 39(9), p. 987-992, 1998.

Bell, E., et al., "Analysis of a cDNA encoding arginine decarboxylase from oat reveals similarity to the *Escherichia coli* arginine decarboxylase and evidence of protein processing", Mol. Gen. Genet. 224, p. 431-436, 1990.

Watson, M., et al. "Regulation of *Arabidopsis thaliana* (L.) Heynh Arginine Decarboxylase by Potassium Deficiency Stress", Plant Physiol. 111, p. 1077-1083, 1996.

Michael, A.J., et al., "Molecular cloning and functional identification of a plant ornithine decarboxylase cDNA", Biochem. J., 314, p. 241-248, 1996.

Mad Arif, S.A., et al., "Characterization of the S-adenosylmethionine decarboxylase (SAMDC) gene of potato", Plant Mol. Biol., 26, p. 324-338, 1994.

Kasukabe, Y., et al, Possibility of Using Polyamine Biosynthesis-related Genes for Improvement of Chilling Tolerance of Plants by Gene Technology.

T. Hatanaka, et al., "Molecular cloning and characterization of coffee cDNA encoding spermidine synthase," Plant Science, vol. 140, pp. 161-168, 1999.

A. Bouchereau, et al., "Polyamines and environmental challenges: recent development," Plant Science, vol. 140, pp. 103-125, 1999.

Kumar A et al, The Plant Journal, vol. 9, No. 2, pp. 147-158, 196.

Capell T, et al, Thereretical and Applied Genetics, vol. 97, pp. 246-254, 1998.

Wi, Soo Jin et al, Plant Biology, vol. 2000, pp. 108, 2000.

Rajam M V et al, Journal of Biosciences, vol. 23, No. 4, pp. 473-482, 1998.

Galston A W et al, Botanica Acts. vol. 110, No. 3, pp. 197-207, 1997.

T. Rorat, et al., "Identification and expression of novel cold induced genes in potato (*Solanum sogarandinum*)," Plant Science, vol. 124, No. 1, pp. 69-78, 1997.

D. Alabadi, et al., "Differential expression of two spermidine synthase genes during early fruit development and in vegetative tissues of pea," Plant Mol. Biol., vol. 39, No. 5, pp. 933-943, 1999.

A. R. Pedros, et al., "Manipulation of S-adenosylmethionine decarboxylase activity in potato tubers," Planta, vol. 209, No. 1, pp. 153-160, 1999.

Chemical Reaction of plant, vol. 35, No. 1, 56-66, 2000.

Kasukabe, Y. et al., "Possibility of Using Polyamine Biosynthesis-related Genes for Improvement of Chilling Tolerance of Plants by Gene Technology," Biotechnology Symposium Abstracts, Sep. 28, 2000, vol. 18, 310-313.

* cited by examiner

1. ROOTS TREATED FOR 6 DAYS AT 23°C
2. ROOTS TREATED FOR 6 DAYS AT 14°C
3. STALKS TREATED FOR 6 DAYS AT 23°C
4. STALKS TREATED FOR 6 DAYS AT 14°C
5. LEAVES TREATED FOR 6 DAYS AT 23°C
6. LEAVES TREATED FOR 6 DAYS AT 14°C

1. ROOTS TREATED FOR 6 DAYS AT 23°C
2. ROOTS TREATED FOR 6 DAYS AT 14°C
3. STALKS TREATED FOR 6 DAYS AT 23°C
4. STALKS TREATED FOR 6 DAYS AT 14°C
5. LEAVES TREATED FOR 6 DAYS AT 23°C
6. LEAVES TREATED FOR 6 DAYS AT 14°C

1. ROOTS TREATED FOR 6 DAYS AT 23°C
2. ROOTS TREATED FOR 6 DAYS AT 14°C
3. STALKS TREATED FOR 6 DAYS AT 23°C
4. STALKS TREATED FOR 6 DAYS AT 14°C
5. LEAVES TREATED FOR 6 DAYS AT 23°C
6. LEAVES TREATED FOR 6 DAYS AT 14°C 1. pBI101—35S—SPDS(+)—Hm2

2. pBI101—35S—SPDS(−)—Hm2

1. WILD TYPE (WT)
2. TRANSFORMANT (TSP-14)
3. TRANSFORMANT (TSP-15)
4. TRANSFORMANT (TSP-16)
5. TRANSFORMANT (TSP-17)
6. TRANSFORMANT (TSP-19)

COMPARISON OF EXTENT OF GROWTH

IN WEEK 6 AFTER INOCULATION

COMPARISON OF EXTENT OF GROWTH

IN WEEK 10 AFTER INOCULATION 1          2

1. WILD TYPE (WT)

2. TRANSFORMANT (T3 HOMOZYGOUS CELL LINE)

SEQUENCE LISTING

<160> NUMBER OF SEQ ID NOS: 12

<210> SEQ ID NO 1
<211> LENGTH: 1328
<212> TYPE: DNA
<213> ORGANISM: Cucurbita ficifolia
<220> FEATURE:
<221> NAME/KEY: CDS
<222> LOCATION: (77)..(1060)

<400> SEQUENCE: 1

```
ccaacgggtc atacagaagc actccccact gtattgggat ttgggatttt agcgagtcga      60
tagtagaggg attatt atg tct gcg gaa cat atc gtt ggg tcg gcg gcc gat     112
               Met Ser Ala Glu His Ile Val Gly Ser Ala Ala Asp
                 1               5                  10 gcg gcg gcg aag aaa cct gag att gag aat ggg gta tcc gcc tca cag       160
Ala Ala Ala Lys Lys Pro Glu Ile Glu Asn Gly Val Ser Ala Ser Gln
         15                  20                  25 ccc gat tct att tcc tct gta att cct gga tgg ttt tct gaa att agc       208
Pro Asp Ser Ile Ser Ser Val Ile Pro Gly Trp Phe Ser Glu Ile Ser
 30                  35                  40 cca atg tgg cct gga gag gcc cat tcc ttg aag gtg gag aag gtt ttg       256
Pro Met Trp Pro Gly Glu Ala His Ser Leu Lys Val Glu Lys Val Leu
 45                  50                  55                  60 ttt caa ggg aag tct gat tac cag aac gtt ttg gta ttt cag tca tca       304
Phe Gln Gly Lys Ser Asp Tyr Gln Asn Val Leu Val Phe Gln Ser Ser
                 65                  70                  75 act tat ggg aag gtt ctg gtt ttg gat ggc gtg att cag ctt aca gag       352
Thr Tyr Gly Lys Val Leu Val Leu Asp Gly Val Ile Gln Leu Thr Glu
             80                  85                  90 aga gat gaa tgt gct tac caa gag atg atc acc cac ctt cca ctt tgc       400
Arg Asp Glu Cys Ala Tyr Gln Glu Met Ile Thr His Leu Pro Leu Cys
         95                 100                 105 tca att cca aac ccc aaa aag gtt ctc gtt atc ggt gga gga gac ggc       448
Ser Ile Pro Asn Pro Lys Lys Val Leu Val Ile Gly Gly Gly Asp Gly
    110                 115                 120 ggt gtt ttg cga gag gtg gct cgc cat tca tct gtt gag cag ata gat       496
Gly Val Leu Arg Glu Val Ala Arg His Ser Ser Val Glu Gln Ile Asp
125                 130                 135                 140 atc tgt gaa atc gac aag atg gta gtt gat gtt tcc aaa gaa ttt ttc       544
Ile Cys Glu Ile Asp Lys Met Val Val Asp Val Ser Lys Glu Phe Phe
                145                 150                 155 cct cgc gta gct gtc ggg ttt gag gat cct cgt gtc act ctt cat att       592
Pro Arg Val Ala Val Gly Phe Glu Asp Pro Arg Val Thr Leu His Ile
            160                 165                 170 ggt gat ggc gtc gca ttt ctg aag gct gtt cct gaa ggc act tat gat       640
Gly Asp Gly Val Ala Phe Leu Lys Ala Val Pro Glu Gly Thr Tyr Asp
        175                 180                 185 gca gtg ata gtg gat tct tct gat cct att ggt cct gca caa gag ctc       688
Ala Val Ile Val Asp Ser Ser Asp Pro Ile Gly Pro Ala Gln Glu Leu
    190                 195                 200 ttt gag aag cct ttt ttt gct tca gtt gcc aaa gct ctt cga cca gga       736
Phe Glu Lys Pro Phe Phe Ala Ser Val Ala Lys Ala Leu Arg Pro Gly
205                 210                 215                 220 ggc gtt gtg tgt act caa gca gag agc att tgg ctt cac atg cat atc       784
Gly Val Val Cys Thr Gln Ala Glu Ser Ile Trp Leu His Met His Ile
                225                 230                 235 att gaa gac att gta aca aac tgc cgc caa ata ttc aaa ggc tct gtc       832
Ile Glu Asp Ile Val Thr Asn Cys Arg Gln Ile Phe Lys Gly Ser Val
```

-continued

```
                     240                 245                 250
aac tat gca tgg act aca gtt cct aca tat cca agc gga gtg att ggg    880
Asn Tyr Ala Trp Thr Thr Val Pro Thr Tyr Pro Ser Gly Val Ile Gly
            255                 260                 265 ttt atg ctc tgc tca act gag ggg cct cct ctt gat ttc aag cat cca    928
Phe Met Leu Cys Ser Thr Glu Gly Pro Pro Leu Asp Phe Lys His Pro
    270                 275                 280 gtc aac cca gta gag gtg aac ggt atc gac acc gtg aag agt ccg ctc    976
Val Asn Pro Val Glu Val Asn Gly Ile Asp Thr Val Lys Ser Pro Leu
285                 290                 295                 300 aag ttt tac aac tcg gag att cat aca gca gct ttc tgt ttg cct tct   1024
Lys Phe Tyr Asn Ser Glu Ile His Thr Ala Ala Phe Cys Leu Pro Ser
                305                 310                 315 ttt gcg aag aag atc atc gat tca aaa gca aaa tga aaggtttcc         1070
Phe Ala Lys Lys Ile Ile Asp Ser Lys Ala Lys
            320                 325 cccacagcgt tgaagaagca gaaattggcg gtcttggagt gtgccaatgt aataagtgga 1130
ggcttaaatt agagtcgaaa tggtcgcttt atattgtgat cagcgtcata agtttcttg  1190 agatgttatg agtagtagaa atagctttg ttttcctccc caaaattttc cccgtccttt  1250
ttcattgaaa agtgacatct ggtgttctag cttctataaa taaatatgct aaataaatat 1310
atttagccaa aaaaaaaa                                               1328
```

<210> SEQ ID NO 2
<211> LENGTH: 327
<212> TYPE: PRT
<213> ORGANISM: Cucurbita ficifolia

<400> SEQUENCE: 2

```
Met Ser Ala Glu His Ile Val Gly Ser Ala Ala Asp Ala Ala Ala Lys
 1               5                  10                  15

Lys Pro Glu Ile Glu Asn Gly Val Ser Ala Ser Gln Pro Asp Ser Ile
            20                  25                  30

Ser Ser Val Ile Pro Gly Trp Phe Ser Glu Ile Ser Pro Met Trp Pro
        35                  40                  45

Gly Glu Ala His Ser Leu Lys Val Glu Lys Val Leu Phe Gln Gly Lys
    50                  55                  60

Ser Asp Tyr Gln Asn Val Leu Val Phe Gln Ser Ser Thr Tyr Gly Lys
65                  70                  75                  80

Val Leu Val Leu Asp Gly Val Ile Gln Leu Thr Glu Arg Asp Glu Cys
                85                  90                  95

Ala Tyr Gln Glu Met Ile Thr His Leu Pro Leu Cys Ser Ile Pro Asn
            100                 105                 110

Pro Lys Lys Val Leu Val Ile Gly Gly Asp Gly Gly Val Leu Arg
        115                 120                 125

Glu Val Ala Arg His Ser Ser Val Glu Gln Ile Asp Ile Cys Glu Ile
    130                 135                 140

Asp Lys Met Val Asp Val Ser Lys Glu Phe Phe Pro Arg Val Ala
145                 150                 155                 160

Val Gly Phe Glu Asp Pro Arg Val Thr Leu His Ile Gly Asp Gly Val
                165                 170                 175

Ala Phe Leu Lys Ala Val Pro Glu Gly Thr Tyr Asp Ala Val Ile Val
            180                 185                 190

Asp Ser Ser Asp Pro Ile Gly Pro Ala Gln Glu Leu Phe Glu Lys Pro
        195                 200                 205
```

-continued

```
Phe Phe Ala Ser Val Ala Lys Ala Leu Arg Pro Gly Val Val Cys
    210                 215                 220

Thr Gln Ala Glu Ser Ile Trp Leu His Met His Ile Ile Glu Asp Ile
225                 230                 235                 240

Val Thr Asn Cys Arg Gln Ile Phe Lys Gly Ser Val Asn Tyr Ala Trp
                245                 250                 255

Thr Thr Val Pro Thr Tyr Pro Ser Gly Val Ile Gly Phe Met Leu Cys
                260                 265                 270

Ser Thr Glu Gly Pro Pro Leu Asp Phe Lys His Pro Val Asn Pro Val
            275                 280                 285

Glu Val Asn Gly Ile Asp Thr Val Lys Ser Pro Leu Lys Phe Tyr Asn
    290                 295                 300

Ser Glu Ile His Thr Ala Ala Phe Cys Leu Pro Ser Phe Ala Lys Lys
305                 310                 315                 320

Ile Ile Asp Ser Lys Ala Lys
                325
```

<210> SEQ ID NO 3
<211> LENGTH: 1814
<212> TYPE: DNA
<213> ORGANISM: Cucurbita ficifolia
<220> FEATURE:
<221> NAME/KEY: CDS
<222> LOCATION: (456)..(1547)

<400> SEQUENCE: 3

```
tccgtctgcg gcctcttgaa ttctcatcgt ttctctctct ttcgaatttt gttttctttc        60
gctctcagcc ctttcttgca agttttattt taggcattct ccgggtttcc ttctcctccg       120
ctaattcttt tcatcgcgaa tgatttaatg gagtcaaaag gtggtaagaa gtctagtagt       180
agtagtagta gaagcagtaa atccctttc tacgaagctc ccctcggata cagcattgaa        240
gacgttagac cacacggtgg aatcaagaag ttcagatctg ctgcctactc caactgcgtt       300
cgtaaaccat cctgagttct gctgaattcc gttttcctg cgcaccgaga tccttagttt        360
tctataattt ttactgtgtc tttttctttt agtactctac tttcctcgtt ctctcgttca       420
atctctcaac attagtaact tccttttaag aaaag atg acg ttt cct acc tct         473
                                     Met Thr Phe Pro Thr Ser
                                       1               5 gca atc gga ttt gaa ggc tat gaa aag agg ctt gaa gta tca ttc ttt         521
Ala Ile Gly Phe Glu Gly Tyr Glu Lys Arg Leu Glu Val Ser Phe Phe
                10                  15                  20 gag ccc ggc att ttt gct gac cca agg ggc atg ggc ctt cgt gct ttg         569
Glu Pro Gly Ile Phe Ala Asp Pro Arg Gly Met Gly Leu Arg Ala Leu
        25                  30                  35 tcc aag gca caa cta gat gaa att ctg aca tta gcc gag tgc acc att         617
Ser Lys Ala Gln Leu Asp Glu Ile Leu Thr Leu Ala Glu Cys Thr Ile
    40                  45                  50 gtt gat tct ttg tcc aat gac tat ctt gat tca tat gtc ctt tcg gag         665
Val Asp Ser Leu Ser Asn Asp Tyr Leu Asp Ser Tyr Val Leu Ser Glu
55                  60                  65                  70 tcg agc ctc ttt gtc tac cca tac aag ttc atc atc aaa act tgc ggc         713
Ser Ser Leu Phe Val Tyr Pro Tyr Lys Phe Ile Ile Lys Thr Cys Gly
                75                  80                  85 act act aag ctg ctt ctg tct att cca gct ctg ata aag ttg gct gat         761
Thr Thr Lys Leu Leu Leu Ser Ile Pro Ala Leu Ile Lys Leu Ala Asp
        90                  95                 100 tct cta tcc ctt aat gtg aaa tct gtg agg tac act cgt gga agc ttt         809
Ser Leu Ser Leu Asn Val Lys Ser Val Arg Tyr Thr Arg Gly Ser Phe
```

```
                    105                 110                 115
atc ttt cct ggt gcc cag tct ttt ccc cat cgc agc ttc tct gag gaa        857
Ile Phe Pro Gly Ala Gln Ser Phe Pro His Arg Ser Phe Ser Glu Glu
120                 125                 130 gtt gct gtt ctt gat ggc tac ttg gcc aag ctt ggc ctc cat ggc tct        905
Val Ala Val Leu Asp Gly Tyr Leu Ala Lys Leu Gly Leu His Gly Ser
135                 140                 145                 150 gct tat gtg atg gga agt cct gat gag aca agg aaa tgg cac gtt tac        953
Ala Tyr Val Met Gly Ser Pro Asp Glu Thr Arg Lys Trp His Val Tyr
                155                 160                 165 tct gcc tgt gcc aaa atg ggt agc cga agc tac aat ccc gtc tat act       1001
Ser Ala Cys Ala Lys Met Gly Ser Arg Ser Tyr Asn Pro Val Tyr Thr
            170                 175                 180 ctg gag atg tgc atg act ggc tta gac aag gag aag gcg tct gtc ttc       1049
Leu Glu Met Cys Met Thr Gly Leu Asp Lys Glu Lys Ala Ser Val Phe
        185                 190                 195 ttc aaa aca gac aca agt tct gct gct gca atg act gaa aac tcc ggt       1097
Phe Lys Thr Asp Thr Ser Ser Ala Ala Ala Met Thr Glu Asn Ser Gly
    200                 205                 210 atc agg aag atc ctt ccg aaa tct gat ata tgc gac ttt gag ttt gac       1145
Ile Arg Lys Ile Leu Pro Lys Ser Asp Ile Cys Asp Phe Glu Phe Asp
215                 220                 225                 230 cca tgt ggg tat tcc atg aat gct att gaa gga gat gcg gag tct acc       1193
Pro Cys Gly Tyr Ser Met Asn Ala Ile Glu Gly Asp Ala Glu Ser Thr
                235                 240                 245 atc cat gtc act cca gaa gaa ggg ttt agc tat gca agc ttt gaa gca       1241
Ile His Val Thr Pro Glu Glu Gly Phe Ser Tyr Ala Ser Phe Glu Ala
            250                 255                 260 gct ggt tat gaa ttg gac gac ctg gac ctg tgt aag gtg att ggg agg       1289
Ala Gly Tyr Glu Leu Asp Asp Leu Asp Leu Cys Lys Val Ile Gly Arg
        265                 270                 275 gtg ctg gca tgc ttc cag cca tct gat ttc tct gtt gcc ctc cac tca       1337
Val Leu Ala Cys Phe Gln Pro Ser Asp Phe Ser Val Ala Leu His Ser
    280                 285                 290 gat gtg gtc ggt gag gat ctg aaa gat tta ctg tgc ctg gac ctg aag       1385
Asp Val Val Gly Glu Asp Leu Lys Asp Leu Leu Cys Leu Asp Leu Lys
295                 300                 305                 310 ggg tac gag ggt gga gag aag agc tgt gaa atg ctt ggg gaa aat gga       1433
Gly Tyr Glu Gly Gly Glu Lys Ser Cys Glu Met Leu Gly Glu Asn Gly
                315                 320                 325 tcc gtc atc tat cag agc ttt aag aat aga gga gat tat gcg tca tct       1481
Ser Val Ile Tyr Gln Ser Phe Lys Asn Arg Gly Asp Tyr Ala Ser Ser
            330                 335                 340 cca agg tca atc ctc atg aaa tgc tgt tgg aga gag gac gag gcg gac       1529
Pro Arg Ser Ile Leu Met Lys Cys Cys Trp Arg Glu Asp Glu Ala Asp
        345                 350                 355 gag gaa gtt gag aag tag tagtagttac ttactttcaa cttttgctgc              1577
Glu Glu Val Glu Lys
    360 gttttatctt ttaatactat agtatcttcg ggtcgttct gttctgtgct gttctgttct      1637 ttcattatgt cctttgtgt tgtttccttt gcgaataata attcccaggt ggggatggta      1697 ggctgtcgtg tcctgtcctg gagagtctat cgtctgatgt tattatgatc atcaaactat     1757 ataatgataa tatcgtattt ccttatttaa aaaaaaaaaa aaaaaaaaaa aaaaaaa        1814

<210> SEQ ID NO 4
<211> LENGTH: 363
<212> TYPE: PRT
<213> ORGANISM: Cucurbita ficifolia
```

<400> SEQUENCE: 4

```
Met Thr Phe Pro Thr Ser Ala Ile Gly Phe Glu Gly Tyr Glu Lys Arg
1               5                   10                  15
Leu Glu Val Ser Phe Phe Glu Pro Gly Ile Phe Ala Asp Pro Arg Gly
            20                  25                  30
Met Gly Leu Arg Ala Leu Ser Lys Ala Gln Leu Asp Glu Ile Leu Thr
        35                  40                  45
Leu Ala Glu Cys Thr Ile Val Asp Ser Leu Ser Asn Asp Tyr Leu Asp
    50                  55                  60
Ser Tyr Val Leu Ser Glu Ser Ser Leu Phe Val Tyr Pro Tyr Lys Phe
65                  70                  75                  80
Ile Ile Lys Thr Cys Gly Thr Thr Lys Leu Leu Leu Ser Ile Pro Ala
                85                  90                  95
Leu Ile Lys Leu Ala Asp Ser Leu Ser Leu Asn Val Lys Ser Val Arg
            100                 105                 110
Tyr Thr Arg Gly Ser Phe Ile Phe Pro Gly Ala Gln Ser Phe Pro His
        115                 120                 125
Arg Ser Phe Ser Glu Glu Val Ala Val Leu Asp Gly Tyr Leu Ala Lys
    130                 135                 140
Leu Gly Leu His Gly Ser Ala Tyr Val Met Gly Ser Pro Asp Glu Thr
145                 150                 155                 160
Arg Lys Trp His Val Tyr Ser Ala Cys Ala Lys Met Gly Ser Arg Ser
                165                 170                 175
Tyr Asn Pro Val Tyr Thr Leu Glu Met Cys Met Thr Gly Leu Asp Lys
            180                 185                 190
Glu Lys Ala Ser Val Phe Phe Lys Thr Asp Thr Ser Ser Ala Ala Ala
        195                 200                 205
Met Thr Glu Asn Ser Gly Ile Arg Lys Ile Leu Pro Lys Ser Asp Ile
    210                 215                 220
Cys Asp Phe Glu Phe Asp Pro Cys Gly Tyr Ser Met Asn Ala Ile Glu
225                 230                 235                 240
Gly Asp Ala Glu Ser Thr Ile His Val Thr Pro Glu Glu Gly Phe Ser
                245                 250                 255
Tyr Ala Ser Phe Glu Ala Ala Gly Tyr Glu Leu Asp Asp Leu Asp Leu
            260                 265                 270
Cys Lys Val Ile Gly Arg Val Leu Ala Cys Phe Gln Pro Ser Asp Phe
        275                 280                 285
Ser Val Ala Leu His Ser Asp Val Val Gly Glu Asp Leu Lys Asp Leu
    290                 295                 300
Leu Cys Leu Asp Leu Lys Gly Tyr Glu Gly Glu Lys Ser Cys Glu
305                 310                 315                 320
Met Leu Gly Glu Asn Gly Ser Val Ile Tyr Gln Ser Phe Lys Asn Arg
                325                 330                 335
Gly Asp Tyr Ala Ser Ser Pro Arg Ser Ile Leu Met Lys Cys Cys Trp
            340                 345                 350
Arg Glu Asp Glu Ala Asp Glu Glu Val Glu Lys
        355                 360
```

<210> SEQ ID NO 5
<211> LENGTH: 3037
<212> TYPE: DNA
<213> ORGANISM: Cucurbita ficifolia
<220> FEATURE:
<221> NAME/KEY: CDS -continued

<222> LOCATION: (541)..(2661)

<400> SEQUENCE: 5

| | |
|---|---:|
| gtttattaaa cgcattctat tgtctctccg agggctctcc aattcttccc gttaggtttc | 60 |
| cgtttgttcc tcttttctc cgcctttttc ccggaaaatc tgtttgttga agcaattgca | 120 |
| tcctcttttg ttttgttttt cttcttttgt tgaatccctg gtttgaattt ttgtgtggat | 180 |
| tctttgattt ccagatctgc atggtgaaga gcggtttcgg tgtttgatgt ttgattggtt | 240 |
| ttgaattcgt agcttgattt ttgtgtttgt tgttatcaaa ttcttcttct gagcggatcg | 300 |
| cggtgggata ttggaagtgt ataggggagc gcggtggatt tgacggtgga aatagctact | 360 |
| ttttttgctt cttttgaggg ggtagccggg gcctcggcct cggcgggttt taaagccccc | 420 |
| acttggacga actctggatt taccattcct ttctcttaac aatttctcta actaatcttt | 480 |
| tcgttttta aattttccgt ctccattttc ttattctttt cttgatccgt cgtcggagag | 540 |

| | | | | | | | | | | | | | | | | |
|---|---|---|---|---|---|---|---|---|---|---|---|---|---|---|---|---:|
| atg | ccg | gcc | cta | gct | tat | tgc | gtg | gaa | gct | gct | gca | gct | cct | cct | cct | 588 |
| Met | Pro | Ala | Leu | Ala | Tyr | Cys | Val | Glu | Ala | Ala | Ala | Ala | Pro | Pro | Pro | |
| 1 | | | | 5 | | | | | 10 | | | | | 15 | | |
| ggc | tgc | gct | ttt | gct | ggg | gat | agc | tct | ctt | ccg | tcg | ccg | gtc | tta | ttt | 636 |
| Gly | Cys | Ala | Phe | Ala | Gly | Asp | Ser | Ser | Leu | Pro | Ser | Pro | Val | Leu | Phe | |
| | | | 20 | | | | | 25 | | | | | 30 | | | |
| tcc | ggc | gga | cct | ccg | gag | act | acc | atc | ttc | acc | tct | ccc | gct | gct | gct | 684 |
| Ser | Gly | Gly | Pro | Pro | Glu | Thr | Thr | Ile | Phe | Thr | Ser | Pro | Ala | Ala | Ala | |
| | | 35 | | | | | 40 | | | | | 45 | | | | |
| ccc | att | tct | gaa | aat | ccc | tct | tgg | tct | cct | tct | ctg | tct | tcc | tcc | ctt | 732 |
| Pro | Ile | Ser | Glu | Asn | Pro | Ser | Trp | Ser | Pro | Ser | Leu | Ser | Ser | Ser | Leu | |
| | 50 | | | | | 55 | | | | | 60 | | | | | |
| tac | aag | ata | gat | gga | tgg | ggt | gcc | cct | tat | ttc | tct | gtc | aat | ggc | tct | 780 |
| Tyr | Lys | Ile | Asp | Gly | Trp | Gly | Ala | Pro | Tyr | Phe | Ser | Val | Asn | Gly | Ser | |
| 65 | | | | | 70 | | | | | 75 | | | | | 80 | |
| ggg | aat | atg | gcc | gtt | cgg | cct | tac | ggt | aca | gcc | acc | ttg | ccc | cat | cag | 828 |
| Gly | Asn | Met | Ala | Val | Arg | Pro | Tyr | Gly | Thr | Ala | Thr | Leu | Pro | His | Gln | |
| | | | 85 | | | | | 90 | | | | | 95 | | | |
| gag | att | gat | ctc | ttg | aaa | att | gtg | aag | aag | gct | tca | gat | ccg | att | agc | 876 |
| Glu | Ile | Asp | Leu | Leu | Lys | Ile | Val | Lys | Lys | Ala | Ser | Asp | Pro | Ile | Ser | |
| | | | 100 | | | | | 105 | | | | | 110 | | | |
| tct | ggt | ggg | ctt | ggc | ttg | cag | ctt | cct | ctt | att | gtg | cgc | ctt | cct | gat | 924 |
| Ser | Gly | Gly | Leu | Gly | Leu | Gln | Leu | Pro | Leu | Ile | Val | Arg | Leu | Pro | Asp | |
| | | 115 | | | | | 120 | | | | | 125 | | | | |
| gtg | ctt | aag | aac | cgt | ttg | gag | tct | ctc | caa | tcg | gca | ttt | gat | tgt | gct | 972 |
| Val | Leu | Lys | Asn | Arg | Leu | Glu | Ser | Leu | Gln | Ser | Ala | Phe | Asp | Cys | Ala | |
| | 130 | | | | | 135 | | | | | 140 | | | | | |
| att | caa | tct | cag | gga | tat | ggg | tct | cat | tac | cag | ggc | gtt | tat | ccg | gtc | 1020 |
| Ile | Gln | Ser | Gln | Gly | Tyr | Gly | Ser | His | Tyr | Gln | Gly | Val | Tyr | Pro | Val | |
| 145 | | | | | 150 | | | | | 155 | | | | | 160 | |
| aaa | tgc | aac | cag | gac | agg | ttc | gtt | gtt | gaa | gac | atc | gtg | aaa | ttc | ggt | 1068 |
| Lys | Cys | Asn | Gln | Asp | Arg | Phe | Val | Val | Glu | Asp | Ile | Val | Lys | Phe | Gly | |
| | | | 165 | | | | | 170 | | | | | 175 | | | |
| tct | cct | ttc | cgt | ttc | ggt | ctc | gag | gct | gga | tcg | aaa | ccg | gag | ctc | ctc | 1116 |
| Ser | Pro | Phe | Arg | Phe | Gly | Leu | Glu | Ala | Gly | Ser | Lys | Pro | Glu | Leu | Leu | |
| | | | 180 | | | | | 185 | | | | | 190 | | | |
| ctg | gca | atg | agc | tgt | ttg | tgc | aaa | ggg | aat | aga | gat | gcc | ctt | ttg | gtg | 1164 |
| Leu | Ala | Met | Ser | Cys | Leu | Cys | Lys | Gly | Asn | Arg | Asp | Ala | Leu | Leu | Val | |
| | | 195 | | | | | 200 | | | | | 205 | | | | |
| tgt | aat | ggt | ttc | aag | gat | gcg | gag | tac | att | tct | ctg | gct | ctt | att | gct | 1212 |
| Cys | Asn | Gly | Phe | Lys | Asp | Ala | Glu | Tyr | Ile | Ser | Leu | Ala | Leu | Ile | Ala | |
| | 210 | | | | | 215 | | | | | 220 | | | | | |
| agg | aag | ctc | gct | ttg | aac | act | gtg | att | gtg | ctt | gaa | caa | gag | gaa | gag | 1260 |

```
Arg Lys Leu Ala Leu Asn Thr Val Ile Val Leu Glu Gln Glu Glu Glu
225                 230                 235                 240 ctt gat ttg gtt atc gat ttg agt aaa acg ctc ttc gtt cgc cct gtg    1308
Leu Asp Leu Val Ile Asp Leu Ser Lys Thr Leu Phe Val Arg Pro Val
                    245                 250                 255 atc ggc atg cgt gcg aag cta aga acc aag cat tct ggt cat ttt ggg    1356
Ile Gly Met Arg Ala Lys Leu Arg Thr Lys His Ser Gly His Phe Gly
                260                 265                 270 tct aca tca ggc gag aaa ggg aaa ttt ggt ctt acg acc aca caa att    1404
Ser Thr Ser Gly Glu Lys Gly Lys Phe Gly Leu Thr Thr Thr Gln Ile
            275                 280                 285 ctt cgt gtg gtt agg aag ctt aaa cag gct gat atg ctt gat tgt ctt    1452
Leu Arg Val Val Arg Lys Leu Lys Gln Ala Asp Met Leu Asp Cys Leu
        290                 295                 300 caa ttg ctc cat ttt cat att ggt tcc cag atc ccc tcc acc gtg tta    1500
Gln Leu Leu His Phe His Ile Gly Ser Gln Ile Pro Ser Thr Val Leu
305                 310                 315                 320 ctc acc gat ggc att agc gag gct gct caa atc tat tgt gaa ttg gtt    1548
Leu Thr Asp Gly Ile Ser Glu Ala Ala Gln Ile Tyr Cys Glu Leu Val
                    325                 330                 335 cgt ctc ggt gcc aac atg cta gtt att gac att gga ggt ggt ctt ggt    1596
Arg Leu Gly Ala Asn Met Leu Val Ile Asp Ile Gly Gly Gly Leu Gly
                340                 345                 350 atc gac tat gac ggg tcg aag tca ggg gat tct gag tta tct gtt gct    1644
Ile Asp Tyr Asp Gly Ser Lys Ser Gly Asp Ser Glu Leu Ser Val Ala
            355                 360                 365 tat gaa ctc gga gag tat gcc tct acg gtt gtt gat gca gtc cgc tgt    1692
Tyr Glu Leu Gly Glu Tyr Ala Ser Thr Val Val Asp Ala Val Arg Cys
        370                 375                 380 gta tgc gac cgt agg gcc gtt aag cac ccg ata att tgc agt gaa agt    1740
Val Cys Asp Arg Arg Ala Val Lys His Pro Ile Ile Cys Ser Glu Ser
385                 390                 395                 400 ggc cga gca atc gtc tct cat cac tct gtt ctg ata ttt gag gct gtt    1788
Gly Arg Ala Ile Val Ser His His Ser Val Leu Ile Phe Glu Ala Val
                    405                 410                 415 tct gct agt tct tat gag gtc cca tcc atg agc tcg att gaa cgt cag    1836
Ser Ala Ser Ser Tyr Glu Val Pro Ser Met Ser Ser Ile Glu Arg Gln
                420                 425                 430 tat ctt gtc gat gga cta acc gac gat gct cgt att gat tat cag aac    1884
Tyr Leu Val Asp Gly Leu Thr Asp Asp Ala Arg Ile Asp Tyr Gln Asn
            435                 440                 445 ctt ttg act gca gct tat atg ggt gag tac aag gcg tgc ttg cta tat    1932
Leu Leu Thr Ala Ala Tyr Met Gly Glu Tyr Lys Ala Cys Leu Leu Tyr
        450                 455                 460 gca gat caa ttg aag caa tgc tgt gtt gag aaa ttc aag gat ggg tgt    1980
Ala Asp Gln Leu Lys Gln Cys Cys Val Glu Lys Phe Lys Asp Gly Cys
465                 470                 475                 480 ttg gga atg gaa gaa cta gct gcg gta gat ggg ctt tgt gcc ctt gtt    2028
Leu Gly Met Glu Glu Leu Ala Ala Val Asp Gly Leu Cys Ala Leu Val
                    485                 490                 495 tca aag gca att gga gag ttg gat gct gta aga act tac cat gtg aac    2076
Ser Lys Ala Ile Gly Glu Leu Asp Ala Val Arg Thr Tyr His Val Asn
                500                 505                 510 ctc tcc att ttc acc tct atc cca gat ttc tgg ggt att gac cag ctg    2124
Leu Ser Ile Phe Thr Ser Ile Pro Asp Phe Trp Gly Ile Asp Gln Leu
            515                 520                 525 ttt cca att gtc cct att cat cgt ctc gat caa aga ccg tca gtg agg    2172
Phe Pro Ile Val Pro Ile His Arg Leu Asp Gln Arg Pro Ser Val Arg
        530                 535                 540
```

| | | |
|---|---|---|
| ggc att cta tcc gat cta acc tgt gac agt gac ggt aag atc gat agg<br>Gly Ile Leu Ser Asp Leu Thr Cys Asp Ser Asp Gly Lys Ile Asp Arg<br>545                     550                       555                    560 | 2220 |
| ttt atc aat ggc gag tcg agc ttg ccg ttg cat gag ctc aaa ggc aac<br>Phe Ile Asn Gly Glu Ser Ser Leu Pro Leu His Glu Leu Lys Gly Asn<br>                565                       570                       575 | 2268 |
| agc agt tta tca ggt gga ggt ggg cga tac tat ctt ggg atg ttt cta<br>Ser Ser Leu Ser Gly Gly Gly Gly Arg Tyr Tyr Leu Gly Met Phe Leu<br>            580                       585                     590 | 2316 |
| ggt ggg gct tat gag gag gct ctc ggt ggt gtt cac aac ctg ttt ggg<br>Gly Gly Ala Tyr Glu Glu Ala Leu Gly Gly Val His Asn Leu Phe Gly<br>595                     600                       605 | 2364 |
| agc ccg agc gtg att cgg gta atg cag agc gat gga ccg cat agc ttt<br>Ser Pro Ser Val Ile Arg Val Met Gln Ser Asp Gly Pro His Ser Phe<br>                610                       615                    620 | 2412 |
| gcg gtg act cgc act gtg cct ggg cca tca tgt gcg gat atc ctc cga<br>Ala Val Thr Arg Thr Val Pro Gly Pro Ser Cys Ala Asp Ile Leu Arg<br>625                     630                       635                    640 | 2460 |
| gtg atg cag tac gag ccc gag ctc atg ttt gag acc ctc aag cat cga<br>Val Met Gln Tyr Glu Pro Glu Leu Met Phe Glu Thr Leu Lys His Arg<br>                645                       650                     655 | 2508 |
| gct gag gag ttt ggg cag gag gag gag gat gat gtt gga ggc att gcc<br>Ala Glu Glu Phe Gly Gln Glu Glu Glu Asp Asp Val Gly Gly Ile Ala<br>            660                       665                     670 | 2556 |
| aat agc ttg gcc atg tcc ttc cgc aac atg cct tat ttg gct agc gca<br>Asn Ser Leu Ala Met Ser Phe Arg Asn Met Pro Tyr Leu Ala Ser Ala<br>675                     680                       685 | 2604 |
| tct tcc tgc gcc aat ggt gct ggc gat gcc gag cag tgg act tac tgc<br>Ser Ser Cys Ala Asn Gly Ala Gly Asp Ala Glu Gln Trp Thr Tyr Cys<br>690                     695                       700 | 2652 |
| tat gct tga tgaataatgt ttgaaggttt agtcgttagc cacatcccta<br>Tyr Ala<br>705 | 2701 |
| aataagctat tggtctgttt tcgttgtcgt ggtcgtcgtc gtcgtaggtc cgtcaacctt | 2761 |
| ttttttttc ttctttggct tgttgcaaag ggttatgaga gcacagcaac agcagccaag | 2821 |
| ctcctcttcc tttggcttta ttttgttta gataggagag gggattagta gaacaccgaa | 2881 |
| tccacccttt tgttaattcg ggatcttgat ctctcttggt tatatcatgg tgtacaactt | 2941 |
| ttaagaagcc gtcaatggct gttttctttt tagatctcaa ctttggatgg ctcaacccca | 3001 |
| cttcgaatta taaaaaaaaa aaaaaaaaaa aaaaaa | 3037 |

<210> SEQ ID NO 6
<211> LENGTH: 706
<212> TYPE: PRT
<213> ORGANISM: Cucurbita ficifolia

<400> SEQUENCE: 6

Met Pro Ala Leu Ala Tyr Cys Val Glu Ala Ala Ala Pro Pro Pro
1               5                   10                   15

Gly Cys Ala Phe Ala Gly Asp Ser Ser Leu Pro Ser Pro Val Leu Phe
                20                       25                       30

Ser Gly Gly Pro Pro Glu Thr Thr Ile Phe Thr Ser Pro Ala Ala Ala
             35                       40                       45

Pro Ile Ser Glu Asn Pro Ser Trp Ser Pro Ser Leu Ser Ser Ser Leu
    50                       55                       60

Tyr Lys Ile Asp Gly Trp Gly Ala Pro Tyr Phe Ser Val Asn Gly Ser
65                  70                      75                    80

```
Gly Asn Met Ala Val Arg Pro Tyr Gly Thr Ala Thr Leu Pro His Gln
                85                  90                  95

Glu Ile Asp Leu Leu Lys Ile Val Lys Lys Ala Ser Asp Pro Ile Ser
            100                 105                 110

Ser Gly Gly Leu Gly Leu Gln Leu Pro Leu Ile Val Arg Leu Pro Asp
            115                 120                 125

Val Leu Lys Asn Arg Leu Glu Ser Leu Gln Ser Ala Phe Asp Cys Ala
130                 135                 140

Ile Gln Ser Gln Gly Tyr Gly Ser His Tyr Gln Gly Val Tyr Pro Val
145                 150                 155                 160

Lys Cys Asn Gln Asp Arg Phe Val Val Glu Asp Ile Val Lys Phe Gly
                165                 170                 175

Ser Pro Phe Arg Phe Gly Leu Glu Ala Gly Ser Lys Pro Glu Leu Leu
                180                 185                 190

Leu Ala Met Ser Cys Leu Cys Lys Gly Asn Arg Asp Ala Leu Leu Val
            195                 200                 205

Cys Asn Gly Phe Lys Asp Ala Glu Tyr Ile Ser Leu Ala Leu Ile Ala
210                 215                 220

Arg Lys Leu Ala Leu Asn Thr Val Ile Val Leu Glu Gln Glu Glu Glu
225                 230                 235                 240

Leu Asp Leu Val Ile Asp Leu Ser Lys Thr Leu Phe Val Arg Pro Val
                245                 250                 255

Ile Gly Met Arg Ala Lys Leu Arg Thr Lys His Ser Gly His Phe Gly
                260                 265                 270

Ser Thr Ser Gly Glu Lys Gly Lys Phe Gly Leu Thr Thr Thr Gln Ile
                275                 280                 285

Leu Arg Val Val Arg Lys Leu Lys Gln Ala Asp Met Leu Asp Cys Leu
            290                 295                 300

Gln Leu Leu His Phe His Ile Gly Ser Gln Ile Pro Ser Thr Val Leu
305                 310                 315                 320

Leu Thr Asp Gly Ile Ser Glu Ala Ala Gln Ile Tyr Cys Glu Leu Val
                325                 330                 335

Arg Leu Gly Ala Asn Met Leu Val Ile Asp Ile Gly Gly Gly Leu Gly
            340                 345                 350

Ile Asp Tyr Asp Gly Ser Lys Ser Gly Asp Ser Glu Leu Ser Val Ala
            355                 360                 365

Tyr Glu Leu Gly Glu Tyr Ala Ser Thr Val Val Asp Ala Val Arg Cys
            370                 375                 380

Val Cys Asp Arg Arg Ala Val Lys His Pro Ile Ile Cys Ser Glu Ser
385                 390                 395                 400

Gly Arg Ala Ile Val Ser His His Ser Val Leu Ile Phe Glu Ala Val
                405                 410                 415

Ser Ala Ser Ser Tyr Glu Val Pro Ser Met Ser Ser Ile Glu Arg Gln
            420                 425                 430

Tyr Leu Val Asp Gly Leu Thr Asp Asp Ala Arg Ile Asp Tyr Gln Asn
            435                 440                 445

Leu Leu Thr Ala Ala Tyr Met Gly Glu Tyr Lys Ala Cys Leu Leu Tyr
450                 455                 460

Ala Asp Gln Leu Lys Gln Cys Cys Val Glu Lys Phe Lys Asp Gly Cys
465                 470                 475                 480

Leu Gly Met Glu Glu Leu Ala Ala Val Asp Gly Leu Cys Ala Leu Val
                485                 490                 495

Ser Lys Ala Ile Gly Glu Leu Asp Ala Val Arg Thr Tyr His Val Asn
```

-continued

```
                    500             505             510
Leu Ser Ile Phe Thr Ser Ile Pro Asp Phe Trp Gly Ile Asp Gln Leu
            515                 520                 525

Phe Pro Ile Val Pro Ile His Arg Leu Asp Gln Arg Pro Ser Val Arg
        530                 535                 540

Gly Ile Leu Ser Asp Leu Thr Cys Asp Ser Asp Gly Lys Ile Asp Arg
545                 550                 555                 560

Phe Ile Asn Gly Glu Ser Ser Leu Pro Leu His Glu Leu Lys Gly Asn
                565                 570                 575

Ser Ser Leu Ser Gly Gly Gly Arg Tyr Tyr Leu Gly Met Phe Leu
            580                 585                 590

Gly Gly Ala Tyr Glu Glu Ala Leu Gly Val His Asn Leu Phe Gly
            595                 600                 605

Ser Pro Ser Val Ile Arg Val Met Gln Ser Asp Gly Pro His Ser Phe
        610                 615                 620

Ala Val Thr Arg Thr Val Pro Gly Pro Ser Cys Ala Asp Ile Leu Arg
625                 630                 635                 640

Val Met Gln Tyr Glu Pro Glu Leu Met Phe Glu Thr Leu Lys His Arg
                645                 650                 655

Ala Glu Glu Phe Gly Gln Glu Glu Asp Val Gly Gly Ile Ala
            660                 665                 670

Asn Ser Leu Ala Met Ser Phe Arg Asn Met Pro Tyr Leu Ala Ser Ala
        675                 680                 685

Ser Ser Cys Ala Asn Gly Ala Gly Asp Ala Glu Gln Trp Thr Tyr Cys
    690                 695                 700

Tyr Ala
705

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 7
gttttggatg gagtgattca                                              20

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 8
gtgaatctca gcgttgta                                                18

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 9
tatgtgctgt ctgagtcgag c                                            21

<210> SEQ ID NO 10
```

-continued

```
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 10
gctaaaccca tcttcagggg t                                          21

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 11
gggctkggar tsgactay                                              18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 12
yccrtcrctg tcrcasgt                                              18
```

PLANT HAVING IMPROVED TOLERANCE TO VARIOUS ENVIRONMENTAL STRESSES, METHOD OF CONSTRUCTING THE SAME AND POLYAMINE METABOLISM-RELATING ENZYME GENE

CROSS REFERENCE TO RELATED APPLICATION

This application is a national stage application of PCT/JP01/07521, filed on Aug. 31, 2001 and claiming priority of JP 2000-285423, filed on Sep. 20, 2000 and JP 2001-32627, filed on Feb. 8, 2001 the contents of which are incorporated herein by reference.

TECHNICAL FIELD

The present invention relates to plants having improved environmental stress tolerance, and in particular to plants having improved cold stress tolerance, salt stress tolerance, herbicide stress tolerance, drought stress tolerance, and osmotic stress tolerance. The present invention further relates a method of producing such plants.

BACKGROUND ART

Plants adapt to various types of environmental stress such as the temperature and salt of their habitats. However, in terms of temperature stress, for example, plants are susceptible to hot or cold temperatures when exposed to environments over or under the maximum or minimum optimum growth temperature, leading to impairment upon the gradual or sudden loss of the physiological functions of cells. Efforts have been made to expand the temperature adaptability of plants by breeding means such as selection or cross breeding in order to make use of wild plants adapted to various temperature environments for food crops, horticultural plants, and the like. The planting period in which vegetables, flowers and ornamental plants, fruit trees, and the like can be cultivated has been expanded by such breeding means as well as by protected horticulture. However, Japan in particular extends a considerable length to the north and south, with extreme variation in climate and considerable change in seasons from area to area, resulting in a greater risk of crop exposure to temperature environments that are not conducive to growth, depending on the area and season. Rice, for example, which originates in tropical regions, can now be cultivated in cooler areas such as the Tohoku district and Hokkaido as a result of improvements in varieties since the Meiji period, and are now cultivated as staples of these regions, but unseasonably low temperatures in early summer in these areas recently have resulted in cold-weather damage, leading to the problem of severe shortages even now. Recently, abnormal atmospheric phenomena attributed to global warming or El Nino have resulted in major crop damage, and the rice shortages caused by severe cold-weather damage in 1993 are still remembered. Culinary plants include many crops of tropical origin among fruits and vegetables such as tomatoes, cucumbers, melons, and water melon. Such crops are in high demand and are extremely important in terms of agriculture, and they have long been involved in greenhouse culture. However, since the oil shock of 1974, the conservation of resources and lowering warming costs have become a problem. The conservation of resources in protected horticulture has been studied from a variety of perspectives, from the structural concerns of green houses to cultivation techniques, but the most basic consideration is increasing the cold tolerance of crops.

In regard to salt stress, it is said that about 10% of all land surface area is salt damaged, and the spread of saline soil, primarily in arid areas such as Southeast Asia and Africa is becoming a serious agricultural problem.

Water stress can be a major form of stress for plants, and is significantly affected by the amount and distribution of precipitation when temperature is not a limiting factor. The growth and yield of crops is tremendously dependent upon drought stress in semi-arid regions and the like which are important areas of crop cultivation.

Cross breeding, breeding making use of recent genetic engineering techniques, methods making use of the action of plant hormones and plant regulators, and the like have been employed to improve tolerance against these various types of environmental stress.

Environmental stress-tolerant plants have thus far been produced using genetic engineering techniques. Genes reported to have been used in the improvement of cold tolerance include fatty acid desaturase genes of membrane lipids (ω-3 desaturase gene, glycerol-3-phosphate acyltransferase gene, and stearoyl-ACP-desaturase gene), pyruvic-phosphate dikinase genes involved in photosynthesis, and genes coding for proteins with cryoprotection/prevention activity (COR15, COR85, and kin1).

Genes reported to have been used in the improvement of tolerance against salt stress and water stress include glycine betaine synthetase genes of osmotic regulators (choline monooxygenase gene and betaine aldehyde hydrogenase gene) and proline synthetase genes (1-pyroline-5-carboxylate synthetase).

Genes reported to have been used in the improvement of tolerance against herbicidal stress include aromatic amino acid synthetase genes (5-enol-pyruvylshikimate-3-phosphate synthase gene) and detoxification enzyme genes (nitrilase gene and phosphinothricin acetyltransferase gene). Although plants involving transformants of such genes have been of some practical use in herbicidal stress-tolerant plants, most have not been effective enough to be used for actual industrial purposes and have not been put to practical use.

Polyamines, the general term for aliphatic hydrocarbons with 2 or more primary amino groups, are ubiquitous natural substances in organisms, with more than 20 types discovered so far. Typical polyamines include putrescine, spermidine, and spermine. The known primary physiological action of polyamines includes (1) nucleic acid stabilization and structural modification through interaction with nucleic acids; (2) promotion of various nucleic acid synthesis systems; (3) activation of protein synthesis systems; and (4) stabilization of cell membranes and enhancement of membrane permeability of substances. Reports on the role of polyamines in plants include cell protection and promotion of nucleic acid or protein biosynthesis during cellular growth or division.

The involvement of polyamines in various types of environmental stress has recently been reported. They have been implicated in cold stress (J. Japan Soc. Hortic. Sci., 68, 780-787 (1999); J. Japan Soc. Hortic. Sci., 68, 967-973 (1999); Plant Physiol. 124, 431-439 (2000)); salt stress (Plant Physiol. 91, 500-504 (1984)); acid stress (Plant Cell Physiol. 38(10), 1156-1166 (1997)); osmotic stress (Plant Physiol. 75, 102-109 (1984)); pathogen infection stress (New Phytol., 135, 467-473 (1997)); and herbicidal stress (Plant Cell Physiol. 39(9), 987-992 (1998)), but all of these reports assume the involvement of polyamines based on the correlation between growth reaction or stress tolerance and changes in polyamine concentration, yet report nothing on their involvement at the genetic level between environmental stress and polyamine metabolism-related enzyme genes coding for polyamine metabolism-related enzymes.

Known polyamine metabolism-related enzymes involved in the biosynthesis of plant polyamines include arginine decarboxylase (ADC), ornithine decarboxylase (ODC), S-adenosylmethionine decarboxylase (SAMDC), spermidine synthase (SPDS), and spermine synthase (SPMS). Several polyamine metabolism-related genes coding for such polyamine metabolism-related enzymes have already been isolated from plants. The ADC gene has been isolated from oats (Mol. Gen., Genet. 224, 431-436 (1990)), tomatoes (Plant Physiol., 103, 829-834 (1993)), *Arabidopsis thaliana* (Plant Physiol., 111, 1077-1083 (1996)), and peas (Plant Mol. Biol., 28, 997-1009 (1995)); the ODC gene has been isolated from datura (Biochem. J., 314, 241-248 (1996)); the SAMDC gene has been isolated from potatoes (Plant Mol. Biol., 26, 327-338 (1994)), spinach (Plant Physiol., 107, 1461-1462 (1995)), and tobacco; and the SPDS gene has been isolated from *Arabidopsis thaliana* (Plant Cell Physiol., 39(1), 73-79 (1998)).

An object of the present invention is thus to undertake biochemical analysis in cultivars having high and low environmental stress tolerance so as to elucidate the mechanism intimately involved in environmental stress tolerance. An object is thus to produce recombinant plants with improved environmental stress tolerance by screening genes that play a major role in this mechanism and by artificially controlling the expression of such genes to lower polyamine levels.

More specifically, the mechanism intimately involved in chilling tolerance is elucidated through biochemical analysis of cultivars having chilling-tolerant and chilling sensitive. Genes playing a major role in this mechanism are obtained. The genes are then applied to actual plants to check the effects at the practical level. Although polyamine metabolism-related genes have been isolated from various plants thus far, there has been little research on the relation between polyamine metabolism-related genes and cold tolerance, and no polyamine metabolism-related genes whose level of expression changes when exposed to low temperature have been found. An object of the invention is thus to provide polyamine metabolism-related genes deeply involved in cold tolerance, and to use such genes to produce plants which are more tolerant to various types of environmental stress such as cold tolerance.

DISCLOSURE OF THE INVENTION

Figure 1:
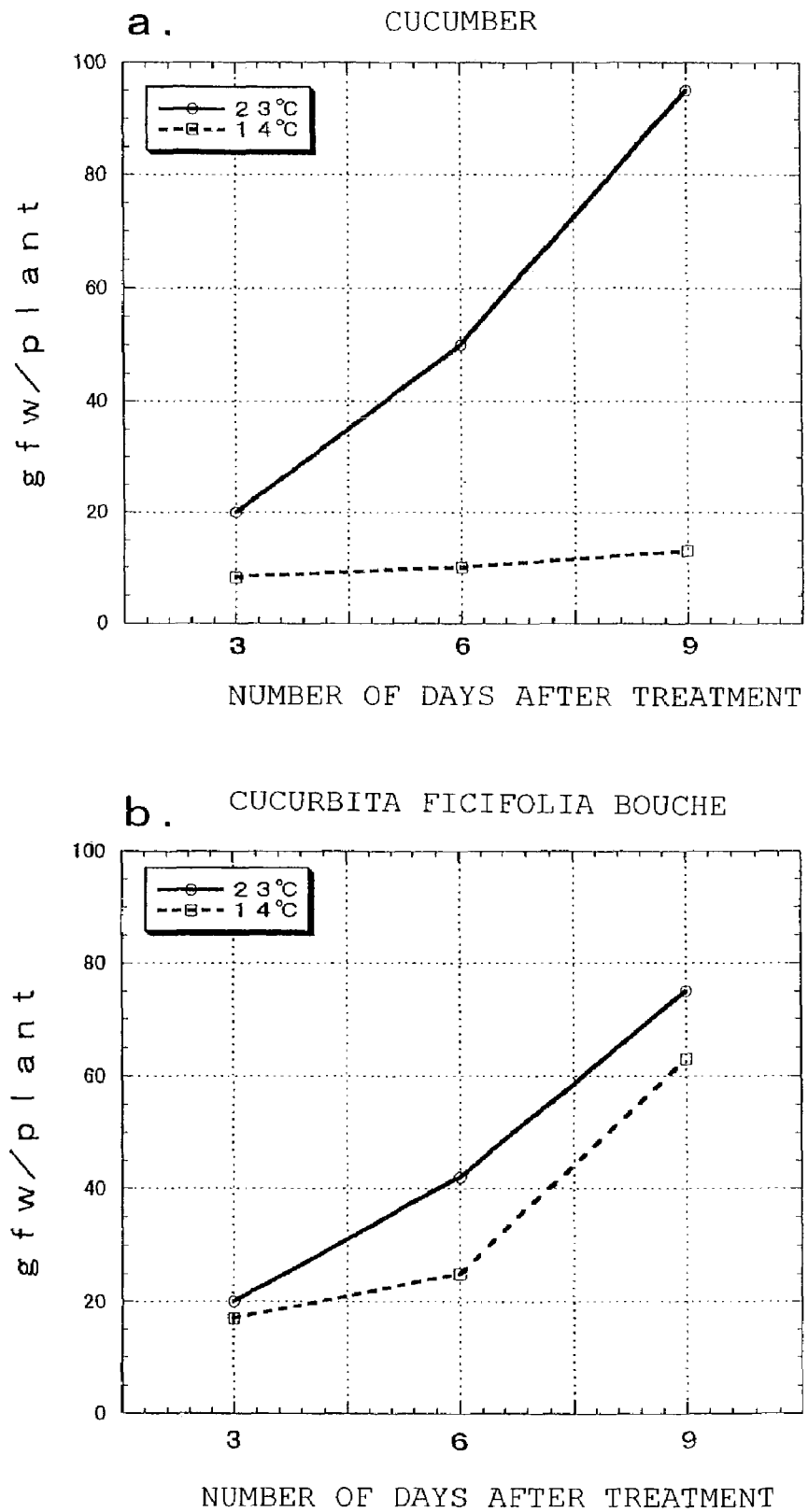
FIG. 1 illustrates the effects of temperature on the root growth of cucumber "Suyo" (FIG. 1A) and *Cucurbita ficifolia* Bouche (FIG. 1B) "gfw" present on the Y-axis means "gram fresh weight of plant."

As a result of extensive research to achieve the aforementioned objects, the inventors discovered that various environmental stress tolerance parameters are improved when polyamine metabolism-related enzyme genes involved in polyamine biosynthesis, whose level of expression changes specifically upon exposure to cold stress, are isolated and are introduced and overexpressed in plants so as to bring about changes in the polyamine concentration through the activation of polyamine metabolism.

Polyamines are basic substances containing an abundance of amines per molecule, typical examples of which include the diamine putrescine, the triamine spermidine, and the quaternary amine spermine. Examples of polyamine metabolism-related enzymes involved in the biosynthesis of such polyamines include ADC and ODC for putrescine, SAMDC and SPDS for spermidine, and SAMDC and SPMS for spermine. Polyamine metabolism-related genes coding for such polyamine metabolism-related enzymes have already been insolated in several plants. However, there have been no reports on plant-derived polyamine metabolism-related enzyme genes whose expression is induced and whose level of expression increases upon exposure to cold stress in plant tissue exhibiting cold stress tolerance.

As a result of extensive research in view of the foregoing to improve the cold stress tolerance of plants, the inventors discovered that the content of the polyamines spermidine and spermine, in particular, increased upon exposure to cold stress in plant tissue exhibiting cold stress tolerance. The inventors actually isolated and identified polyamine metabolism-related genes (SPDS, SAMDC, ADC) involved in spermidine and spermine biosynthesis from plant tissue exhibiting cold stress tolerance, and discovered that the expression of three of the polyamine metabolism-related genes was induced and that their level of expression was increased upon exposure to cold stress, revealing that these genes were deeply involved in cold stress tolerance. The inventors perfected the present invention upon discovering that the introduction and over-expression of these genes in plants brought about changes in the polyamine concentration through the activation of polyamine metabolism.

The present invention is intended to provide the following.

1. Plants and their progeny, which retain an exogenous polyamine metabolism-related enzyme gene or genes in a stable manner under the control of a promoter or promoters capable of functioning in plants, and the resulting plants and their progeny have an improved environmental stress tolerance more than plants lacking said exogenous polyamine metabolism-related enzyme gene or genes.

2. Plants and their progeny according to 1, wherein the plants with improved environmental stress tolerance comprise transformants obtained by the transformation of plants lacking said exogenous polyamine metabolism-related enzyme gene or genes with an expression vector containing said polyamine metabolism-related enzyme gene or genes under the control of a promoter or promoters capable of functioning in plants.

3. Plants and their progeny according to 1, wherein the polyamine metabolism-related enzyme genes are at least one selected from the group consisting of genes coding for arginine decarboxylase (ADC), genes coding for ornithine decarboxylase (ODC), genes coding for S-adenosylmethionine decarboxylase (SAMDC), genes coding for spermidine synthase (SPDS), and genes coding for spermine synthase (SPMS).

4. Plants and their progeny according to 3, wherein the polyamine metabolism-related enzyme gene is a gene coding for spermidine synthase.

5. Plants and their progeny according to 1, wherein the polyamine metabolism-related enzyme gene is a spermidine synthase gene comprising a base sequence of (a), (b), or (c) below:

(a) the base sequence represented by base numbers 77 through 1060 in the base sequence given in SEQ ID NO. 1 of the sequence listing (SPDS, 1328);

(b) a base sequence coding for a protein with spermidine synthase activity and hybridizing under stringent conditions with the base sequence of (a) above; and (c) a base sequence coding for a protein with spermidine synthase activity, comprising the base sequence of (a) or (b) with 1 or more bases deleted, substituted, inserted, or added.

6. Plants and their progeny according to 1, wherein the polyamine metabolism-related enzyme gene is an S-adenosylmethionine decarboxylase gene comprising a base sequence of (a), (b), or (c) below:

(a) the base sequence represented by base numbers 456 through 1547 in the base sequence given in SEQ ID NO. 3 of the sequence listing (SAMDC, 1814);

(b) a base sequence coding for a protein with S-adenosylmethionine decarboxylase activity and hybridizing under stringent conditions with the base sequence of (a) above; and (c) a base sequence coding for a protein with S-adenosylmethionine decarboxylase activity, comprising the base sequence of (a) or (b) with 1 or more bases deleted, substituted, inserted, or added.

7. Plants and their progeny according to 1, wherein the polyamine metabolism-related enzyme gene is an arginine decarboxylase gene comprising a base sequence of (a), (b), or (c) below:

(a) the base sequence represented by base numbers 541 through 2661 in the base sequence given in SEQ ID NO. 5 of the sequence listing (ADC, 3037);

(b) a base sequence coding for a protein with arginine decarboxylase activity and hybridizing under stringent conditions with the base sequence of (a) above; and (c) a base sequence coding for a protein with arginine decarboxylase activity, comprising the base sequence of (a) or (b) with 1 or more bases deleted, substituted, inserted, or added.

8. Plants and their progeny according to 1, comprising plants with improved cold stress tolerance.

9. Plants and their progeny according to 1, comprising plants with improved salt stress tolerance.

10. Plants and their progeny according to 1, comprising plants with improved herbicidal stress tolerance.

11. Plants and their progeny according to 1, comprising plants with improved drought stress tolerance.

12. Plants and their progeny according to 1, comprising plants with improved osmotic stress tolerance.

13. Plants and their progeny according to 1, comprising dicotyledons.

14. Plants and their progeny according to 1, which are in the form of flowers, fruits, seeds, fibers, or calli.

15. Leaves, stems, flowers, ovaries, fruit, seeds, or calli obtained from plants and their progeny according to any of 1 through 6.

16. Useful substances obtained form plants and their progeny according to any of 1 through 6.

17. A method for producing plants with improved environmental stress tolerance than plants lacking an exogenous polyamine metabolism-related enzyme gene, comprising the step of transforming cells of a plant in which the exogenous polyamine metabolism-related enzyme gene or genes are retained in a stable manner under the control of a promoter capable of functioning in plants and which is lacking said exogenous polyamine metabolism-related enzyme gene or genes.

18. A method for producing plants with improved environmental stress tolerance more than plants lacking an exogenous polyamine metabolism-related enzyme gene, comprising the step of transforming cells of a plant lacking said exogenous polyamine metabolism-related enzyme gene with an expression vector containing the exogenous polyamine metabolism-related enzyme gene or genes under the control of a promoter or promoters capable of functioning in plants.

19. A method according to 18, further comprising the step of regenerating plants from the transformants.

20. A method according to 18, wherein the polyamine metabolism-related enzyme gene or genes are at least one selected from the group consisting of genes coding for arginine decarboxylase (ADC), genes coding for ornithine decarboxylase (ODC), genes coding for S-adenosylmethionine decarboxylase (SAMDC), genes coding for spermidine synthase (SPDS), and genes coding for spermine synthase (SPMS).

21. A method according to 18, wherein the polyamine metabolism-related enzyme gene is a spermidine synthase gene comprising a base sequence of (a), (b), or (c) below:

(a) the base sequence represented by base numbers 77 through 1060 in the base sequence given in SEQ ID NO. 1 of the sequence listing (SPDS, 1328);

(b) a base sequence coding for a protein with spermidine synthase activity and hybridizing under stringent conditions with the base sequence of (a) above; and (c) a base sequence coding for a protein with spermidine synthase activity, comprising the base sequence of (a) or (b) with 1 or more bases deleted, substituted, inserted, or added.

22. A method according to 18, wherein the polyamine metabolism-related enzyme gene is an S-adenosylmethionine decarboxylase gene comprising a base sequence of (a), (b), or (c) below:

(a) the base sequence represented by base numbers 456 through 1547 in the base sequence given in SEQ ID NO. 1;

(b) a base sequence coding for a protein with S-adenosylmethionine decarboxylase activity and hybridizing under stringent conditions with the base sequence of (a) above; and (c) a base sequence coding for a protein with S-adenosylmethionine decarboxylase activity, comprising the base sequence of (a) or (b) with 1 or more bases deleted, substituted, inserted, or added.

23. A method according to 18, wherein the polyamine metabolism-related enzyme gene is an arginine decarboxylase gene comprising a base sequence of (a), (b), or (c) below:

(a) the base sequence represented by base numbers 541 through 2661 in the base sequence given in SEQ ID NO. 1;

(b) a base sequence coding for a protein with arginine decarboxylase activity and hybridizing under stringent conditions with the base sequence of (a) above; and (c) a base sequence coding for a protein with arginine decarboxylase activity, comprising the base sequence of (a) or (b) with 1 or more bases deleted, substituted, inserted, or added.

24. A method according to 18, wherein the plants with improved environmental stress tolerance comprise plants with improved cold tolerance.

25. A method according to 18, wherein the plants with improved environmental stress tolerance comprise plants with improved salt stress tolerance.

26. A method according to 18, wherein the plants with improved environmental stress tolerance comprise plants with improved herbicidal stress tolerance.

27. A method according to 18, wherein the plants with improved environmental stress tolerance comprise plants with improved drought stress tolerance.

28. A method according to 18, wherein the plants with improved environmental stress tolerance comprise plants with improved osmotic stress tolerance.

29. A method according to 18, wherein the plants with improved environmental stress tolerance comprise dicotyledons.

30. A method for producing a plant with fixed traits, which is a homozygote with respect to an exogenous polyamine metabolism-related enzyme gene or genes and which has improved environmental stress tolerance more than plants lacking said exogenous polyamine metabolism-related enzyme gene, comprising the steps of:

(1) transforming cells of plants lacking said exogenous polyamine metabolism-related enzyme gene in a vector containing the exogenous polyamine metabolism-related enzyme gene or genes under the control of a promoter or promoters capable of functioning in plants;

(2) regenerating plants with improved environmental stress tolerance more than plants lacking said exogenous polyamine metabolism-related enzyme gene from the transformants;

(3) harvesting seeds by pollination from the plant bodies; and (4) assaying the polyamine metabolism-related enzyme genes in the seeds obtained by pollination from the plant bodies, which have been obtained by cultivation of the seeds.

31. A method for producing calli with fixed traits, which is a homozygote with respect to the polyamine metabolism-related enzyme gene or genes and which has improved environmental stress tolerance more than plants lacking said exogenous polyamine metabolism-related enzyme gene, comprising the steps of:

(1) transforming cells of plants lacking said exogenous polyamine metabolism-related enzyme gene in a vector containing the exogenous polyamine metabolism-related enzyme gene or genes under the control of a promoter or promoters capable of functioning in plants; and (2) deriving calli from the transformants.

32. A method for selecting transformed plants which grow better than plants lacking an exogenous polyamine metabolism-related enzyme gene or genes, by transforming plants with said exogenous polyamine metabolism-related enzyme gene or genes under the control of a promoter or promoters capable of functioning in plants to allow them to grow after transformation under conditions of environmental stress.

33. A method for selecting transformed plants without the use of a drug resistance marker, by transforming a plant with an exogenous polyamine metabolism-related enzyme gene or genes and another exogenous gene under the control of a promoter or promoters capable of functioning in plants to allow them to grow after transformation under conditions of environmental stress.

34. An isolated plant-derived polyamine metabolism-related enzyme gene, whose level of expression changes when exposed to environmental stress.

35. A gene according to 34, wherein the polyamine metabolism-related enzyme gene comprises a gene coding for arginine decarboxylase (ADC), a gene coding for ornithine decarboxylase (ODC), a gene coding for S-adenosylmethionine decarboxylase (SAMDC), a gene coding for spermidine synthase (SPDS), or a gene coding for spermine synthase (SPMS).

36. A gene according to 34, wherein the polyamine metabolism-related enzyme gene is a spermidine synthase gene comprising a base sequence of (a), (b), or (c) below:

(a) the base sequence represented by base numbers 77 through 1060 in the base sequence given in SEQ ID NO. 1 of the sequence listing (SPDS, 1328);

(b) a base sequence coding for a protein with spermidine synthase activity and hybridizing under stringent conditions with the base sequence of (a) above; and (c) a base sequence coding for a protein with spermidine synthase activity, comprising the base sequence of (a) or (b) with 1 or more bases deleted, substituted, inserted, or added.

37. A gene according to 34, wherein the polyamine metabolism-related enzyme gene is an S-adenosylmethionine decarboxylase gene comprising a base sequence of (a), (b), or (c) below:

(a) the base sequence represented by base numbers 456 through 1547 in the base sequence given in SEQ ID NO. 3 of the sequence listing (SAMDC, 1814);

(b) a base sequence coding for a protein with S-adenosylmethionine decarboxylase activity and hybridizing under stringent conditions with the base sequence of (a) above; and (c) a base sequence coding for a protein with S-adenosylmethionine decarboxylase activity, comprising the base sequence of (a) or (b) with 1 or more bases deleted, substituted, inserted, or added.

38. A gene according to 34, wherein the polyamine metabolism-related enzyme gene is an arginine decarboxylase gene comprising a base sequence of (a), (b), or (c) below:

(a) the base sequence represented by base numbers 541 through 2661 in the base sequence given in SEQ ID NO. 5 of the sequence listing (ADC, 3037);

(b) a base sequence coding for a protein with arginine decarboxylase activity and hybridizing under stringent conditions with the base sequence of (a) above; and (c) a base sequence coding for a protein with arginine decarboxylase activity, comprising the base sequence of (a) or (b) with 1 or more bases deleted, substituted, inserted, or added.

39. A gene according to 34, wherein the plant is a dicotyledon.

40. A gene according to 34, wherein the plant is a monocotyledon.

41. A gene according to 34, wherein the plant is a Cucurbitaceae.

42. A gene according to 34, wherein the plant is *Cucurbita ficifolia* Bouche.

43. Antisense DNA or antisense RNA to a gene according to any of 34 through 42.

44. A recombinant plasmid, characterized by containing a gene according to any of 34 through 42.

45. Transformants containing a plasmid according to 44.

46. Microbes characterized by being transformed in a plasmid containing a plant-derived polyamine metabolism-related enzyme gene whose level of expression changes when exposed to low temperatures.

47. Transformed microbes according to 46, wherein the transformed microbes are *E. coli* or *Agrobacterium* cells.

48. A plant, characterized by being transformed with a plasmid containing a plant-derived polyamine metabolism-related enzyme gene whose level of expression changes when exposed to low temperatures.

49. A transformed plant according to 48, wherein the transformed plant is *Arabidopsis thaliana*.

50. Leaves, stems, flowers, ovaries, fruit, seeds, fibers, or callus obtained from transformants, plants and their progeny according to 45.

51. Useful substances obtained from transformants, plants and their progeny according to 45.

As used in the present invention, "environmental stress" refers to stress received from the environment, such as high temperatures, low temperatures, low pH, low oxygen, oxidation, osmotic, drought, cadmium, ozone, air pollution, UV rays, pathogens, salt, herbicides, intense light, flooding, and pests.

As used in the present invention, "plants lacking an exogenous polyamine metabolism-related enzyme gene" mean any plants genomically lacking said exogenous polyamine metabolism-related enzyme gene. As such, wild species, as well as cultivated varieties established through common cross breeding, natural or artificial variants thereof, transgenic plants incorporating exogenous genes other than polyamine metabolism-related enzyme genes, and the like are all included.

The "polyamines" referred to in the present invention are common natural substances ubiquitous in organisms, and are aliphatic hydrocarbon compounds with two or more primary amine groups. Examples include 1,3-diaminopropane, putrescine, cadaverine, carvine, spermidine, homospermidine, aminopropylcadaverine, thermine, spermine, thermospermine, canavalmine, aminopentylnorspermidine, N,N-bis(aminopropyl)cadaverine, homospermine, caldopentamine, homocaldopentamine, caldohexamine, and homocaldohexamine.

Polyamine Metabolism-related Enzyme Genes

As used in the present invention, "polyamine metabolism-related enzyme genes" are genes coding for amino acids of enzymes involved in polyamine biosynthesis in plants. Examples which are believed to be involved, and to be rate limiting, include arginine decarboxylase (ADC) and ornithine decarboxylase (ODC) genes for the typical polyamine putrescine, S-adenosylmethionine decarboxylase (SAMDC) and spermidine synthase (SPDS) genes for spermidine, and S-adenosylmethionine decarboxylase (SAMDC) and spermine synthase (SPMS) genes for spermine.

Arginine decarboxylase (ADC: EC4.1.1.19.) is an enzyme catalyzing the reaction producing agmatine and carbon dioxide from L-arginine. Ornithine decarboxylase (ODC: EC4.1.1.17.) is an enzyme catalyzing putrescine and carbon dioxide from L-ornithine. S-adenosylmethionine decarboxylase (SAMDC: EC4.1.1.50.) is an enzyme catalyzing the reaction producing adenosylmethylthiopropylamine and carbon dioxide from S-adenosylmethionine. Spermidine synthase (SPDS: EC2.5.1.16.) is an enzyme catalyzing the reaction producing spermidine and methylthioadenosine from putrescine and adenosylmethylthiopropylamine.

These genes, any of which may be derived, can be isolated from various plants. Specific examples include dicotyledons such as Cucurbitaceae; Solanaceae; Brassicaceae such as *Arabidopsis thaliana*; Papilionaceae such as alfalfa and *Vigna unguiculata*; Malvaceae; and Asteraceae; or monocotyledons such as gramineae, including wheat, barley, and corn. Drought-resistant cactus or *Mesembryanthemum crystallinum* are also included. Cucurbitaceae are preferred, and *Cucurbita ficifolia* Bouche is especially preferred.

Plant tissue in which the plant-derived polyamine metabolism-related enzyme genes of the invention are isolated may be in the form of seeds or in the process of growing. The genes may be isolated from part or all of the tissue of growing plants. Any part can be used to isolate genes, but whole plants, buds, flowers, ovaries, fruit, leaves, stems, roots, and the like are preferred. Parts that are tolerant to environmental stress are especially desirable.

Preferred examples of polyamine metabolism-related enzyme genes used in the present invention include the spermidine synthase gene, S-adenosylmethionine decarboxylase (SAMDC), and arginine decarboxylase gene. Specific examples include:

DNA having the base sequence represented by base numbers 77 through 1060 in the base sequence given in SEQ ID NO. 1;

DNA having the base sequence represented by base numbers 456 through 1547 in the base sequence given in SEQ ID NO. 3; and DNA having the base sequence represented by base numbers 541 through 2661 in the base sequence given in SEQ ID NO. 5.

Further examples include:

DNA having a base sequence capable of hybridizing under stringent conditions with any of the above sequences, and coding for a polypeptide with polyamine metabolism-related enzyme activity equivalent to those sequences.

Still further examples include:

DNA comprising any of the above base sequences with 1 or more bases deleted, substituted, inserted, or added, and coding for a polypeptide with polyamine metabolism-related enzyme activity equivalent to those sequences.

The "stringent conditions" referred to here mean conditions under which only base sequences coding for a polypeptide with polyamine metabolism-related enzyme activity equivalent to the polyamine metabolism-related enzyme encoded by a specific polyamine metabolism-related enzyme gene sequence form hybrids with the specific sequence (referred to as specific hybrids), and base sequences coding for polypeptides with no such equivalent activity do not form hybrids with the specific sequence (referred to as non-specific hybrids). One with ordinary skill in the art can readily select such conditions by varying the temperature during the hybridization reaction and washing process, the salt concentration during the hybridization reaction and washing process, and so forth. Specific examples include, but are not limited to, conditions under which hybridization is brought about at 42° C. in 6×SSC (0.9 M NaCl, 0.09 M trisodium citrate) or 6×SSPE (3M NaCl, 0, 2 M NaH$_2$PO$_4$, 20 mM EDTA-2Na, pH 7.4), and the product is washed with 0.5×SSC at 42° C.

The "base sequences with 1 or more bases deleted, substituted, inserted, or added" referred to here are widely known by those having ordinary skill in the art to sometimes retain physiological activity even when the amino acid sequence of a protein generally having that physiological activity has one or more amino acids substituted, deleted, inserted, or added. Genes that have such modifications and that code for a polyamine metabolism-related enzyme are included within the scope of the present invention. For example, the poly A tail or 5',3' end nontranslation regions may be "deleted," and bases may be "deleted" to the extent that amino acids are deleted. Bases may also be "substituted," as long as no frame shift results. Bases may also be "added" to the extent that amino acids are added. However, it is essential that such modifications do not result in the loss of polyamine metabolism-related enzyme activity. "Genes with one or more bases deleted, substituted, or added" are preferred.

Such modified DNA can be obtained by modifying the DNA base sequences of the invention so that amino acids at specific sites are substituted, deleted, inserted, or added by site-specific mutagenesis, for example (Nucleic Acid Research, Vol. 10, No. 20, 6487-6500 (1982)).

In the present invention, "antisense genes" mean genes with a sequence complementary to the base sequence of a plant-derived polyamine metabolism-related enzyme gene whose level of expression changes when exposed to cold stress. Antisense DNA is complementary the base sequence of SEQ ID NOS. 1, 3, or 5, for example. Antisense RNA is produced from that.

Plants and Progeny with Improved Environmental Stress Tolerance

As noted above, in the present invention, "environmental stress" includes stress received from the environment, such as high temperatures, low temperatures, low pH, low oxygen, oxidation, osmotic, drought, cadmium, ozone, air pollution, UV rays, pathogens, salt, herbicides, intense light, flooding, and pests. Of these, "cold stress" is stress on plants due to exposure of the plants to environments below the minimum optimal growth temperature of the plant. Plants subject to cold stress are damaged as a result of gradual or sudden loss of cellular physiological function. "Salt stress" is stress on plants due to exposure of the plants to environments over the maximum optimal growth salt concentration of the plant. Plants subject to salt stress are damaged as a result of gradual or sudden loss of cellular physiological function due to intracellular infiltration of excess salt. "Herbicidal stress" is stress on plants due to exposure of the plants to environments over the maximum optimal growth herbicide concentration of the plant. Plants subject to herbicidal stress are damaged as a result of gradual or sudden loss of cellular physiological function. "Drought stress" is stress on plants due to exposure of the plants to environments under the minimum optimal growth moisture concentration of the plant. Plants subject to drought stress are damaged as a result of gradual or sudden loss of cellular physiological function. "Osmotic stress" is stress on plants due to exposure of the plants to environments over or under the maximum or minimum optimal growth osmotic of the plant. Plants subject to osmotic stress are damaged as a result of gradual or sudden loss of cellular physiological function.

In the present invention, "plants with improved environmental stress tolerance" and "plants having improved environmental stress tolerance" refer to plants in which the introduction of an exogenous polyamine metabolism-related enzyme gene provides or improves environmental stress tolerance compared to before the gene was introduced. Because polyamines are involved in various types of environmental stress (such as high temperatures, low pH, low oxygen, oxidation, osmotic, drought, cadmium, ozone, air pollution, UV rays, pathogens, and pests) tolerance, these types of environmental stress tolerance can be improved. Examples include, but are not limited to, plants to which the introduction of a polyamine metabolism-related enzyme gene results in improved cold stress resistance (tolerance), salt stress resistance (tolerance), herbicide stress resistance (tolerance), drought stress resistance (tolerance), or osmotic resistance (tolerance) compared to plants lacking such an exogenous polyamine metabolism-related enzyme gene.

Specifically, "plants with improved cold stress tolerance" are plants in which limited growth or damage caused by cold stress during the growth of the plant can be avoided or diminished. "Plants with improved salt stress tolerance" are plants in which limited growth or damage caused by salt stress during the growth of the plant can be avoided or diminished. "Plants with improved herbicidal stress tolerance" are plants in which limited growth or damage caused by herbicidal stress during the growth of the plant can be avoided or diminished. "Plants with improved drought stress tolerance" are plants in which limited growth or damage caused by drought stress during the growth of the plant can be avoided or diminished. "Plants with improved osmotic stress tolerance" are plants in which limited growth or damage caused by osmotic stress during the growth of the plant can be avoided or diminished. As a result, more stable cultivation, greater productivity and yields, and greater cultivation areas and surface area can be expected. The use of lower amounts of herbicides and the use of a broader range of stable herbicides can also be expected of "plants with improved herbicidal stress tolerance."

The plants of the invention include not only the plant in its entirety (whole plant), but also calli, seeds, all plant tissue, leaves, stems, roots, flowers, fruits, and fibers. Their progeny are also included in the plants of the invention.

"Useful substances obtained from plants and their progeny" in the present invention indicate useful substances produced by plants and their progeny in which the introduction of an exogenous polyamine metabolism-related enzyme gene provides or improves environmental stress tolerance compared to before the gene was introduced. Examples of useful substances include amino acids, oils and lipids, starch, protein, phenols, hydrocarbons, cellulose, natural rubber, dyes, enzymes, antibodies, vaccines, medicinal products, and biodegradable plastics.

The plants of the present invention are plants with no exogenous polyamine metabolism-related enzyme gene, to which such an exogenous polyamine metabolism-related enzyme gene is introduced by genetic engineering and is retained in a stable manner. As used herein, "retained in a stable manner" means that the polyamine metabolism-related enzyme gene is expressed in the plant at least in which the polyamine metabolism-related enzyme gene has been introduced, and is retained in the plant cells long enough to result in the improvement of environmental stress tolerance. The polyamine metabolism-related enzyme gene is, therefore, preferably incorporated on the chromosomes of the host plant. The polyamine metabolism-related enzyme gene or genes should even more preferably be retained in subsequent generations.

As used herein, "exogenous" means not intrinsic to the plant, but externally introduced. Accordingly, an "exogenous polyamine metabolism-related enzyme gene" may be a polyamine metabolism-related enzyme gene homologous to the host plant (that is, derived from the host plant), which is externally introduced by genetic manipulation. The use of a host-derived polyamine metabolism-related enzyme gene is preferred in consideration of the identity of the codon usage.

The exogenous polyamine metabolism-related enzyme gene may be introduced into plants by any method of genetic engineering. Examples include protoplast fusion with heterologous plant cells having the polyamine metabolism-related enzyme gene, infection with a plant virus having a viral genome genetically manipulated to express the polyamine metabolism-related enzyme gene, or transformation of host plant cells using an expression vector containing the polyamine metabolism-related enzyme gene.

The plants of the invention are preferably transgenic plants which are obtained by the transformation of cells of plants lacking the exogenous polyamine metabolism-related enzyme gene in an expression vector containing the exogenous polyamine metabolism-related enzyme gene under the control of a promoter capable of functioning in plants.

Examples of promoters capable of functioning in plants include the 35S promoter of the cauliflower mosaic virus (CaMV) which is structurally expressed in plant cells, the nopaline synthase gene (NOS) promoter, octopine synthase gene (OCS) promoter, phenylalanine ammonia lyase (PAL) gene promoter, and chalcone synthase (CHS) gene promoter. Other well-known plant promoters not limited to these are also available.

Not only promoters constitutively expressed in the entire organ such as the 35S promoter, but also promoters regulated by low temperature, elevated temperature, stress, drought, light, heat, hormones, damage or the like can be used to express the target gene according to the living environment. For example, a polyamine metabolism-related enzyme gene and a promoter capable of transcription only when the plant is exposed to low temperatures (such as the BN115 promoter: Plant Physiol., 106, 917-928 (1999)) can be used to control the polyamine metabolism of the plant only at low temperatures and to improve the cold stress resistance. A polyamine metabolism-related enzyme gene and a promoter capable of transcription only when the plant is exposed to drought (such as the Atmyb2 promoter: The Plant Cell, 5, 1529-1539, 1993) can also be used to control the polyamine metabolism of the plant during drought and to improve the drought stress resistance.

An organ- or tissue-specific promoter can also be used to express the target gene only in specific organs or tissue.

The exogenous polyamine metabolism-related enzyme gene in the expression vector of the present invention is located downstream of the promoter so that transcription is controlled by the promoter capable of functioning in plants. A transcription termination signal (terminator region) capable of functioning in plants should also be added downstream of the polyamine metabolism-related enzyme gene. An example is the terminator NOS (nopaline synthase) gene.

The expression vector of the present invention may also contain a cis-regulatory element such as an enhancer sequence. The expression vector may also contain a marker gene for selecting transformants such as a drug-resistance gene marker, examples of which include the neomycin phosphotransferase II (NPTII) gene, the phosphinothricin acetyl transferase (PAT) gene, and the glyophosate resistance gene. Because the incorporated gene is sometimes dropped in the absence of selection pressure, it is advantageous to ensure that a herbicide resistance gene is also present on the vector so that the use of a herbicide during cultivation will always result in conditions involving selection pressure.

To facilitate mass production and purification, the expression vector should also contain a selection marker gene (such as ampicillin resistance gene or tetracycline resistance gene) in $E.\ coli$ and a replication origin capable of autonomous replication in $E.\ coli$. The expression vector of the present invention can be constructed in a simple manner by inserting the selection marker gene as needed and an expression cassette of the polyamine metabolism-related enzyme gene at the cloning site of an $E.\ coli$ vector (pUC or pBR series).

When the exogenous polyamine metabolism-related enzyme gene is introduced by infection with $Agrobacterium$ $tumefaciens$ or $Agrobacterium$ $rhizogenes$, the polyamine metabolism-related enzyme gene expression cassette can be inserted in the T-DNA region (region transferred to plant chromosome) on a Ti or Ri plasmid of the cells. At present, binary vector systems are used in standard methods of transformation with $Agrobacterium$. The necessary functions for T-DNA transfer are independently provided by both the T-DNA itself and the Ti (or Ri) plasmid, these structural elements being divided on separate vectors. The binary plasmid has 25 bp border sequences at both ends necessary for cleaving and combining the T-DNA, and the plant hormone gene inducing crown gall (or hairy root) is removed, simultaneously providing room for inserting the exogenous gene. Examples of commercially available binary vectors include pBI101 and pBI121 (both by Clontech). The Vir region involved in the incorporation of the T-DNA has trans action on the separate Ti (or Ri) plasmid referred to as the helper plasmid.

Various conventionally known methods can be used for the transformation of the plants. Examples include the PEG method in which protoplasts are isolated from plant cells by treatment with a cell wall-degrading enzyme such as cellulase or hemicellulase, and polyethylene glycol is added to a suspension of the protoplasts and an expression vector containing the aforementioned polyamine metabolism-related enzyme gene expression cassette to incorporate the expression vector into the protoplasts by a process such as endocytosis; the liposome method in which an expression vector is introduced by ultrasonic treatment or the like into lipid membrane vesicles such as phosphatidylcholine, and the vesicles are fused with protoplasts in the presence of PEG; methods of fusion in a similar process using micelles; and electroporation in which electrical pulses are applied to a suspension of protoplasts and an expression vector to incorporate the vectors in the external solution into the protoplasts. However, these methods are complicated in that they require a culturing technique for the redifferentiation of the protoplasts into plants. Processes for introducing the gene into intact cells with cell walls include direct injection such as microinjection in which a micropipette is inserted into cells to inject the vector DNA in the pipettes under hydraulic or gas pressure into the cells, or the particle gun method in which metal microparticles coated with DNA are accelerated through the detonation of an explosive or gas pressure and thus introduced into the cells, and methods involving the use of infection with *Agrobacterium*. Drawbacks of microinjection are the need for considerable training and the small number of cells that are handled. It is therefore more desirable to transform plants with more convenient methods such as the *Agrobacterium* method and the particle gun method. The particle gun method is useful in that genes can be directly introduced into the apical meristem of plants while cultivated. In the *Agrobacterium* method, the genomic DNA of a plant virus such as the tomato golden mosaic virus (TGMV) or another gemini virus is simultaneously inserted between the border sequences into the binary vector, so that the viral infection can spread throughout the entire plant and the target gene can be simultaneously introduced into the entire plant simply by inoculating cells at any location of the cultivated plant with the viral cell suspension.

Specific examples of methods for obtaining polyamine metabolism-related enzyme genes as well as methods for introducing the target gene using *Agrobacterium* to produce transformants are given below.

1. Obtaining Polyamine Metabolism-related Enzyme Genes (1) Preparation of cDNA Library for Cold Stress Induction PCR poly(A) $^+$RNA is extracted in the usual manner from root tissue of *Cucurbita ficifolia* Bouche which has undergone 3 days of low temperature treatment at 18° C. daytime/14° C. night time. A cDNA library can be prepared for use in PCR from the isolated poly(A) $^+$RNA using a commercially available marathon cDNA Amplification Kit (by Clontech) or the like. The isolated poly(A) $^+$RNA is used as template, and reverse transcriptase and modified lock-docking oligo (dT) primer with two degenerate nucleotide positions at the 3' end are used to synthesize the first-strand cDNA. Double-stranded cDNA is obtained by polymerase reaction. The double-stranded cDNA is blunted with T4 DNA polymerase, and a Marathon cDNA adapter is ligated, giving a library of double-stranded cDNA with the adapter added.

(2) Design of PCR Primer

The SPDS gene, SAMDC gene, ADC gene, and ODC gene can be isolated as the polyamine metabolism-related enzyme gene. The SPDS gene can be isolated from *Cucurbita ficifolia* Bouche or *Hyoscyamus niger*, the SAMDC gene can be isolated from potatoes, spinach, or tobacco, the ADC gene can be isolated from soybean, peas, or tomatoes, and the ODC gene can be isolated from Datura. The base sequences have already been determined. Extremely well conserved regions can therefore be selected by comparing known base sequences, and DNA oligomers can be synthesized to design primers for PCR.

(3) Obtaining SPDS Gene, SAMDC Gene, and ADC Gene Fragments by PCR

The cDNA library for PCR prepared in (1) above is used as template, and the primers designed in (2) above are used to carry out PCR. The PCR products are isolated by gel electrophoresis and are purified with glass milk or the like. The purified PCR products are ligated to a cloning vector such as the TA vector.

The base sequences of the cloned cDNA are determined by the method of Maxam-Gilbert, the dideoxy method, or the like. Either method can be carried out using commercially available kits, and an auto sequencer can be used for automatic sequencing.

(4) Isolation of Full-Length Gene

The full-length gene can be obtained in the usual manner by plaque hybridization, RACE (rapid amplification of cDNA ends), Marathon RACE, or the like.

(5) Northern Analysis

To make sure that the level of expression of the plant-derived polyamine metabolism-related enzyme gene obtained above changes when specifically exposed to cold stress in tissue exhibiting cold stress resistance, RNA is isolated from the roots of *Cucurbita ficifolia* Bouche exhibiting cold stress resistance and from the tissue of leaves or stems lacking cold stress resistance which have been treated at a low temperature of 14° C. and the optimal temperature of 23° C., and Northern hybridization is brought about using the above obtained gene as probe so as to check that the gene's level of expression specifically changes in roots that have cold stress resistance when exposed to cold stress.

The resulting gene will be involved in polyamine biosynthesis, its expression will be specifically higher in tissue that has cold stress resistance when exposed to cold stress, and the gene will be deeply involved in such cold stress resistance. The skillful use of the gene, that is, the molecular biological control of the gene's expression, will enable the production of plants with enhanced cold stress resistance. The simultaneous control of the polyamine levels will enable the production of plants in which various other forms of environmental stress resistance, not just cold stress resistance, can be enhanced.

2. Introduction of Target Gene with *Agrobacterium* into *Arabidopsis thaliana*, and Preparation of Transformed Plant The genes obtained in 1. above can be introduced into a plant host to produce transgenic plants with resistance against various types of stress such as salt stress, herbicidal stress, drought stress, or osmotic stress, and not just cold stress (including freezing stress) in particular.

(1) Preparation of Expression Construct and Transformation of *Agrobacterium*

Expression constructs can be prepared by cleaving the polyamine metabolism-related enzyme gene obtained in 1. above with suitable restriction enzymes so as to include all of the open reading frame, then ligating suitable linkers as needed, and inserting the gene into a plant transformation vector. Examples of plant transformation vectors which can be used include pBI101 and pBI121.

The resulting expression construct is amplified in *E. coli*, and the expression construct is then transformed by tripartite conjugation (Nucleic Acid Research, 12, 8711 (1984)), freeze thawing, electroporation, or the like with *Agrobacterium tumefaciens* C58, LBA4404, EHA101, or the like. Tripartite conjugation involves, for example, the culture of *E. coli* having an expression construct containing the target gene, *E. coli* having a helper plasmid (such as pRK2013), and *Agrobacterium* on medium containing an antibiotic (such as rifampicillin, kanamycin, or hygromycin) so as to obtain transformed *Agrobacterium*.

(2) Production of Transgenic Plant

Parts of plants to which genes can be introduced in the present invention include the entire plant, plant organs (such as leaves, stems, roots, flower organs, vegetative points, and seeds), plant tissue (such as bark, phloem, soft tissue, wood, and vascular bundle), and plant cultured cells.

The target gene can be introduced upon infecting plants with the transformed *Agrobacterium* prepared in (1) by callus regeneration (Plant Cell Reports, 12, 7-11 (1992)), for example. That is, MSO plates (4.6 g Murashige-Skoog mineral salts, 10 g sucrose, 1 mL/L of 1000×vitamin stock, pH 6.2) can be inoculated with seeds of *Arabidopsis*

*thaliana* in the usual manner for aseptic culture. After taking root, slices of root can be used in the culture of callus on CIM plates (MSO plates supplemented with 2,4-dichlorophenoxyacetic acid to a final concentration of 0.5 μg/mL and kinetin to a final concentration of 0.05 μg/mL). *Agrobacterium* transformed with plasmid containing the target gene joined to the promoter, kanamycin and hygromycin resistance genes is cultured, diluted samples are aliquoted into tubes, and slices of the roots on which callus is forming are soaked for several days of co-cultivation on CIM plates.

When the strains have grown enough to become visible to the naked eye, they are disinfected for several days of culture on SIMC plates (MSO plates supplemented with N6-[2-isopentenyl]adenine to a final concentration of 5 μg/mL, indoleacetic acid (IAA) to a final concentration of 0.15 μg/mL, and claforan to a final concentration of 500 μg/mL). The slices are finally cultured on SIMCS plates (plates containing kanamycin and hygromycin) and repeatedly transplanted to fresh plates every week. The transformed slices continue to be grown, resulting in callus. Slices that have not been transformed will turn brown, as the selection is based on antibiotics. The transformants are about 5 mm, and are cultured until rosette leaves are formed. When the complete rosette form is evident, the roots of the transformants are cut with a scalpel to leave out the callus and are transplanted to RIM plates (MSO plates supplemented with IAA to a final concentration of 0.5 μg/mL). When large calli are attached, the roots will show through the callus even if they have taken root, and vascular bundles will not often become joined to the rosettes. After about 8 to 10 days, they become planted on rock wool soaked with mineral salts (5 mM $KNO_3$, 2.5 mM K-phosphate buffer (pH 5.5), 2 mM $MgSO_4$, 2 mM $Ca(NO_3)_2$, 50 μM Fe-EDTA, 1000×microelements (70 mM $H_3BO_3$, 14 mM $MnCl_2$, 0.5 mM $CuSO_4$, 1 mM $ZnSO_4$, 0.2 mM $NaMoO_4$, 10 mM NaCl, 0.01 mM $CoCl_2$) 1 mL/L). Plants that have flowered and formed pods are transplanted to soil soaked with mineral salt media, allowing the seeds to be obtained. The seeds are disinfected and are allowed to germinate upon the inoculation of MSH (MSO plates supplemented with hygromycin to a final concentration of 5 U/mL), thereby allowing transformants to be obtained.

Plants can be infected with the transformed *Agrobacterium* prepared in (1) by infiltration at reduced pressure (The Plant Journal, 19(3), 249-257 (1999)) to introduce the target gene. That is, potting compost (such as METROMIX®) is inoculated with seeds of *Arabidopsis thaliana*, which are cultivated under conditions involving long days (such as 16 hour days and 8 hour nights) at 22° C. After about 3 to 4 weeks, the extended main axis (flower stalk) is cut to begin induction of lateral shoots. After about 1 week of top pruning, the *Arabidopsis thaliana* is dipped in a suspension of cultured *Agrobacterium* transformants, is placed in a dessicator, which is suctioned with a vacuum pump to about −0.053 MPa (400 mmHg), and is then allowed to stand at ambient temperature for 10 minutes. The infected pot is transferred to a deep-bottomed tray and tilted on its side to allow a small amount of water to drip into the bottom of the tray, a transparent covering is placed on it, and it is then allowed to stand for about 1 day under humid conditions. The infected pot is then raised, and cultivation is started under conditions involving long days at 22° C. to harvest the seeds.

The seeds are harvested for about 2 to 4 weeks, and the harvested seeds are strained through a tea strainer or the like to remove debris and husks, and are dried and stored in a dessicator.

The selection of transgenic plants involves sterilizing the harvested seeds in the usual manner and suspending them in about 9 mL of 0.1% agar aqueous solution, then spreading the suspension on selection medium (such as 1×MS salt, 1×Gamborg B5 vitamin, 1% sucrose, 0.5 g/L MES, 0.8% agar, 100 mg/L carbenicillin, 50 mg/L kanamycin, 40 mg/L hygromycin) for aseptic culture at 22° C. Transgenic plants showing resistance to the antibiotics will grow well and can be identified in about 1 to 2 weeks. Transgenic plants with about 4 to 6 true leaves are transplanted to pots containing potting compost to begin cultivation during long days at 22° C.

DNA is extracted in the usual manner from the resulting transgenic plants, the DNA is cleaved with suitable restriction enzymes, and the polyamine metabolism-related enzyme gene can be used as probe in Southern hybridization to determine whether or not the gene has been introduced.

RNA can be extracted in the usual manner from transgenic or non-transgenic plants to prepare probes with the polyamine metabolism-related enzyme gene sense sequence or antisense sequence, and the probes can be used in Northern hybridization to study the expression of the target gene.

Because the polyamine metabolism-related enzyme genes of the invention undergo changes in the level of their expression when exposed to cold stress and are involved in cold stress resistance, their base sequences can be used as markers during cold stress to elucidate the mechanism of cold stress resistance and to enable isolation of regulatory genes (promoter sequences) functionally expressed during cold stress. Accordingly, the use of the base sequence of such genes as markers during cold stress may allow the mechanism of cold stress resistance or cold tolerance to be elucidated, and may allow genes regulating such resistance to be isolated.

Callus can be induced from the resulting transgenic plants to produce callus.

The proportion of transformed progeny T2, created by self-pollination, of transgenic plants (T1) obtained by reduced pressure infiltration will ordinarily follow Mendel's laws. For example, when the polyamine metabolism-related enzyme gene is heterozygously incorporated in a gene locus, the proportion of transformants in T2 progeny will be 3:1. In terms of T3 progeny produced by self-pollination upon cultivation of T2 progeny, when transformants appear in all progeny, the T2 transformed plants will be homozygotes, and when transformants are isolated in a proportion of 3:1, the T2 transformed plants will be heterozygotes with respect to the introduced polyamine metabolism-related enzyme gene.

Plants which are homozygotes with respect to the introduced polyamine metabolism-related enzyme gene which has been thus selected will be extremely useful in the field of seed production as a line in which the improved environmental stress tolerance is fixed.

The polyamine content and type of environmental stress tolerance can be evaluated in transgenic plants in which the genetic expression of polyamine metabolism-related enzyme genes has been analyzed by Southern or Northern analysis as described above.

In the case of polyamine assay, for example, 5% perchloric acid aqueous solution is added to 0.05 to 1 g sample to extract the polyamine. Assay of the extracted polyamines involves fluorescent labeling by benzoylation, dansylation, or the like, followed by analysis with an internal standard using high performance liquid chromatography (HPLC) with a UV detector.

Cold stress tolerance, for example, can be evaluated by low temperature treatment for 1 to 5 days at −10 to 15° C., followed by growth at 20 to 25° C. to study the state of growth, low temperature damage, or the like. Salt stress tolerance can be evaluated by studying the state of growth, salt stress damage, or the like following growth at 20 to 25° C. on medium containing 10 to 300 mM NaCl. Herbicidal stress tolerance can be evaluated by studying the state of growth (germination percentage, survival rate, etc.) or the like following growth at 20 to 25° C. on medium containing 0.2 to 3 μM paraquat. Drought stress tolerance can be evaluated by studying the state of growth and the extent of damage after the supply of water has been terminated. Osmotic stress tolerance can be evaluated by studying the state of growth, osmotic stress damage, and the like after growth at 20 to 25° C. on medium containing 50 to 500 mM sorbitol.

Examples of plants which may be transformed in the invention include, but are not limited to, dicotyledons, monocotyledons, herbaceous plants, and shrubs. Examples include sweet potatoes, tomatoes, cucumbers, squash, melons, watermelon, tobacco, *Arabidopsis thaliana*, bell peppers, eggplant, beans, taro, spinach, carrots, strawberries, white potatoes, rice, corn, alfalfa, wheat, barley, soybeans, rapeseed, sorghum, Eucalyptus, poplar, kenaf, *Eucommia ulmoides*, sugarcane, *Chenopodium album*, lilies, orchids, carnations, roses, petunias, *Torenia fournieri*, sunflowers, *Zoisia japonica*, cotton, matsutake mushrooms, shiitake mushrooms, mushrooms, ginseng, citrus fruits, bananas, and kiwi fruit. Sweet potatoes, tomatoes, cucumbers, rice, corn, soybeans, wheat, Eucalyptus, and cotton are preferred.

Plants with improved environmental stress tolerance in the present invention can be used (grown) not only in regions subject to environmental stress but also in regions devoid of such environmental stress because they will be able to withstand unexpected environmental stress, but they may also be used exclusively in areas subject to environmental stress.

The present invention can improve various types of environmental stress tolerance in plants, can prevent damage or alleviate limited growth caused by various types of environmental stress which plants may encounter during their growth, and can be expected to result in more stable cultivation, improve productivity, expand areas of cultivation, and the like.

BEST MODE FOR CARRYING OUT THE INVENTION

The invention is illustrated in further detail by the following examples, but they are provided only as examples and do not in any way limit the scope of the invention.

EXAMPLE 1

Measurement of Polyamine Content in Roots of Cucumbers and *Cucurbita ficifolia* Bouche (1) Preparation of Samples

*Cucurbita ficifolia* Bouche having high cold stress resistance in the roots and cucumber "Suyo" having poor cold stress resistance were planted in glass rooms, and were transplanted to pots filled with commercially available fine soil (Sansan soil, by Takii & Co., Ltd.) at the cotyledon development stage. At the first leaf stage, the plants were placed in artificial ventilation rooms (air temperature: day 26° C./night 20° C.; relative humidity: day 70%/night 85%; light intensity: 480 μM/m$^2$s; 15 hour long day). Nine each were planted in two cultivation tanks (1/2-fold Hoagland's solution 1201; night temperature: 23° C.).

(2) Low Temperature Treatment 4 days after planting, the live weight of each was determined, they were replanted, and the night temperature of one cultivation tank was lowered to 14° C.

(3) Sampling

Following the low temperature treatment, three at a time were harvested every 3 days, and the live weight of the stems and roots was determined. 5 g of roots was also prepared for polyamine assay and stored frozen at −80° C. until analysis.

(4) Assay of Polyamine Content

Polyamines were extracted from leaves with 5% perchloric acid aqueous solution (4 mL per 1.0 g sample live weight). Diluted internal standard solutions of putrescine, spermidine, and spermine were added, and the samples were then centrifuged at 2° C. for 20 minutes at 40,000×g. The supernatant was then applied on a cation exchange resin (50W-4X, 200-400 mesh, H+ type (by Biorad)) column. The column was flushed with 0.7 N NaCl/0.1 M sodium phosphate buffer (pH 8.0), water, and 1 N hydrochloric acid, in that order, to eliminate amino acids and organic materials other than polyamines. 6 N hydrochloric acid was added to the column, which was drained until no liquid came out, and polyamines were recovered. The eluate was dried at reduced pressure at 40° C., and 5% perchloric acid was added to dissolve the polyamines. Assay of the polyamines putrescine, spermidine, and spermine involved analysis with an internal standard by HPLC with a UV detector following benzoylation. The HPLC column was an Inertsil ODS-2 (4.6×250 mm; by GL Science), and the eluant was 58% methanol containing 1% acetic acid.

The root growth and polyamine content of *Cucurbita ficifolia* Bouche and cucumbers during exposure to cold stress were determined in the manner described above. The results are given in FIGS. 1 through 4.

The results in FIG. 1 show that the growth of the cucumber roots with poor cold stress resistance was clearly inhibited by the 14° C. low temperature treatment, but that the root growth of *Cucurbita ficifolia* Bouche having high low stress resistance was somewhat lower than at 23° C.

Figure 2:
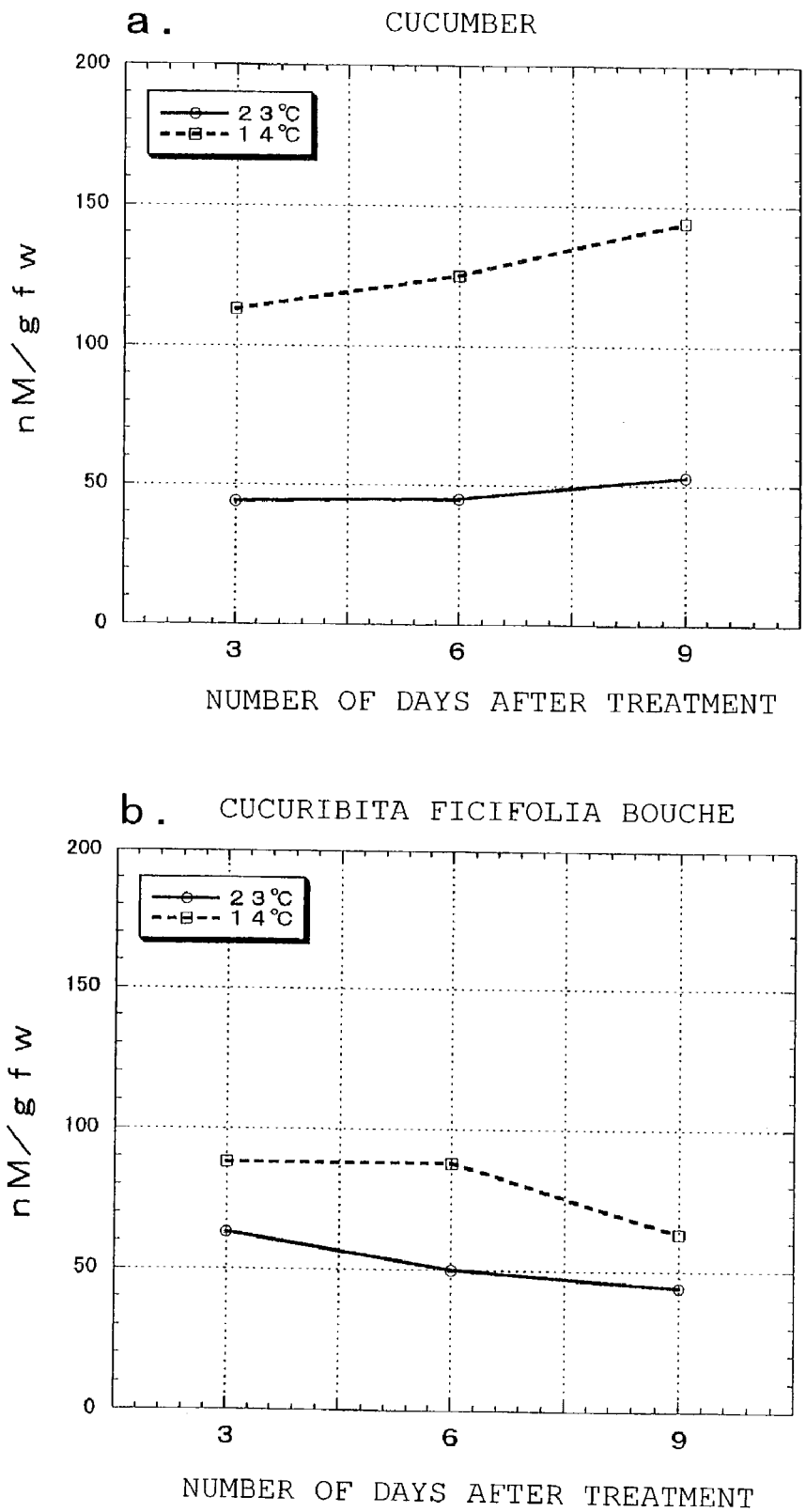
FIG. 2 illustrates the effects of temperature on the putrescine concentration in the roots of cucumber "Suyo" (FIG. 2A) and *Cucurbita ficifolia* Bouche (FIG. 2B) "nM/gfw" present on the Y-axis means "nM putrescine per gram fresh weight of plant."

The results of FIG. 2 show that the putrescine concentration in both crops was higher at the low temperature of 14° C. than at 23° C.

Figure 3:
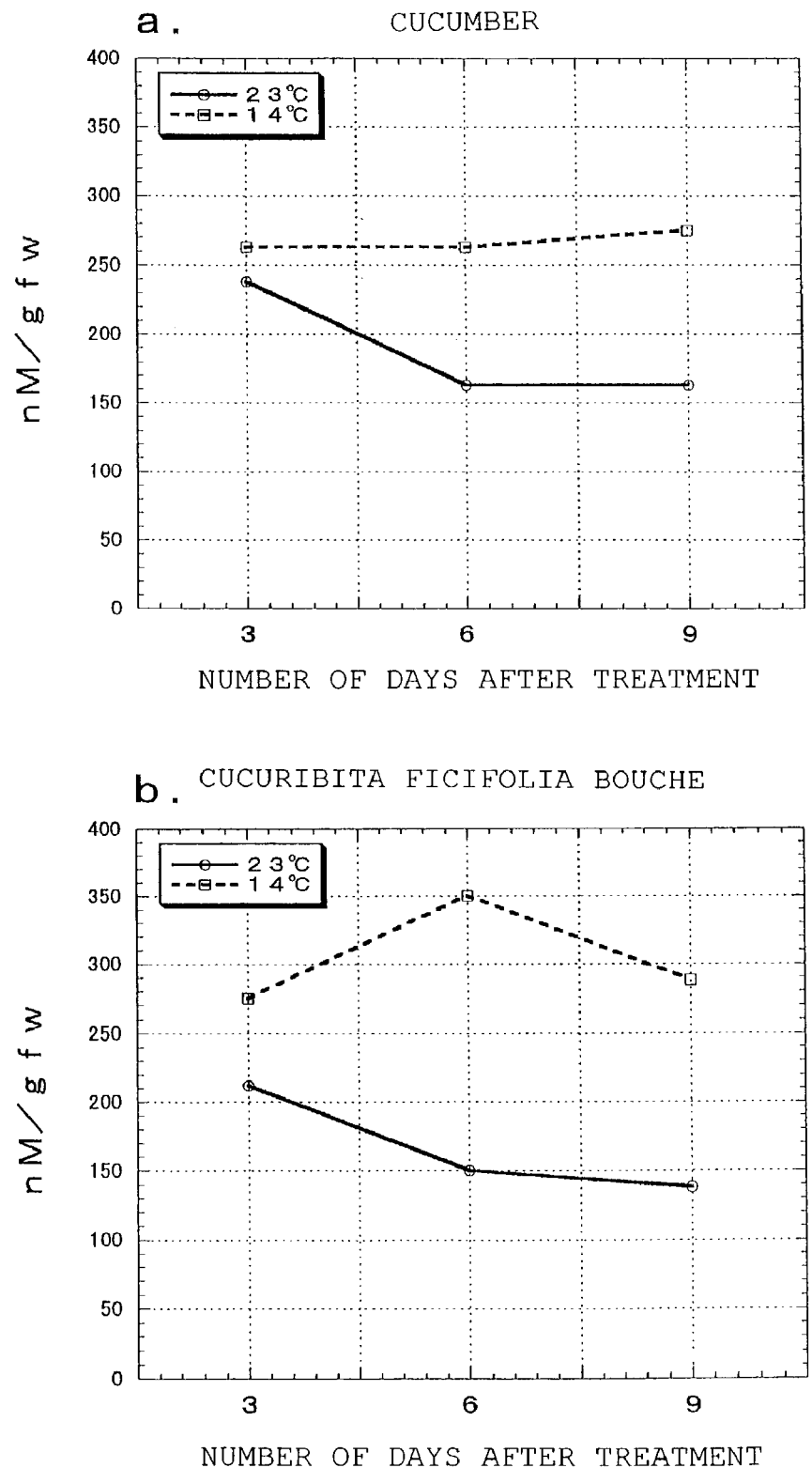
FIG. 3 illustrates the effects of temperature on the spermidine concentration in the roots of cucumber "Suyo" (FIG. 3A and *Cucurbita ficifolia* Bouche (FIG. 3B) "Nm/gfw" present on the Y-axis means nM spermidine per gram fresh weight of plant."

The results of FIG. 3 show that the spermidine concentration in both crops was higher at the low temperature of 14° C. than at 23° C., but that there was a greater difference between 14° C. and 23° C. in the *Cucurbita ficifolia* Bouche having higher cold stress resistance.

Figure 4:
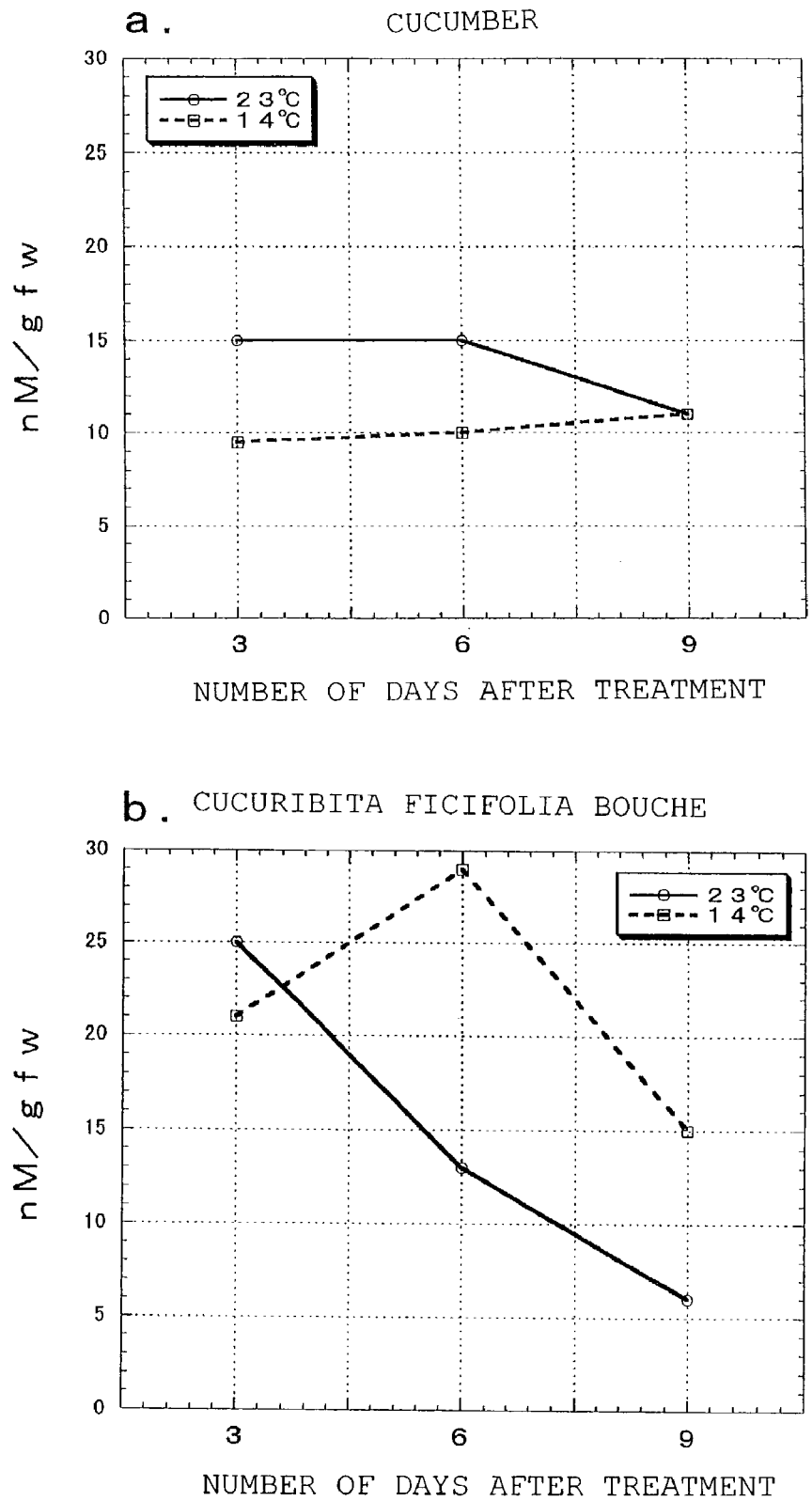
FIG. 4 illustrates the effects of temperature on the spermine concentration in the roots of cucumber "Suyo" (FIG. 4A) and *Cucurbita ficifolia* Bouche (FIG. 4B) "nM/gfw" present on the Y-axis means nM spermidine per gram fresh weight of plant."

The results of FIG. 4 show that the spermine concentration was higher at 23° C. in cucumbers, whereas it was higher at 14° C. than at 23° C. in the *Cucurbita ficifolia* Bouche on days 6 and 9 of the low temperature treatment.

The results of the experiments confirmed higher levels of polyamines, particularly spermidine and spermine, at the low temperature of 14° C. than at 23° C. in the roots of *Cucurbita ficifolia* Bouche having high cold stress resistance. This suggests that polyamines are intimately related to the cold stress resistance of the roots of *Cucurbita ficifolia* Bouche, and that the quantitative changes in polyamine levels are important. The increase in the level of polyamines at the low temperature of 14° C. in the roots of *Cucurbita ficifolia* Bouche, which has high cold stress resistance, is attributed to the activation of polyamine metabolism as a result of the low temperature-induced expression of the polyamine metabolism-related enzyme gene involved in polyamine biosynthesis in the roots.

EXAMPLE 2

Cloning of Plant-Induced Polyamine Metabolism-Related Enzyme Gene (1) Preparation of Poly(A)+ RNA Vermiculite was inoculated with *Cucurbita ficifolia* Bouche, and the plants were transplanted to pots filled with commercially available fine soil (Sansan soil, by Takii & Co., Ltd.) at the cotyledon development stage. The potted *Cucurbita ficifolia* Bouche was placed in incubators (air temperature: day 26° C./night 22° C., 13 hour long days) for plant cultivation. At the two leaf stage, the incubator temperature was lowered to day 18° C./night 14° C. to begin low temperature treatment. After 3 days of low temperature treatment, the plants were divided into roots, stems, and leaves for sampling. The samples were stored in an −80° C. freeze until RNA extraction.

About 4 g of *Cucurbita ficifolia* Bouche root tissue was immediately frozen in liquid nitrogen and finely milled in a mortar and pestle in the presence of liquid nitrogen. 10 mL of 0.2 M Tris acetic acid buffer (5 M guanidine thiocyanate, 0.7% β-mercaptoethanol, 1% polyvinyl pyrrolidone (M.W. 360,000), 0.62% N-lauroylsarcosine sodium salt, pH 8.5) for extraction was then added, and the tissue was milled for 2 minutes while cooled on ice using a Polytron homogenizer (by Kinematica). The mercaptoethanol and polyvinyl pyrrolidone were added just before use. The milled product was then centrifuged for 20 minutes at 17,000×g, and the supernatant was recovered.

The supernatant was filtered through mira cloth, the filtrate was gently layered in 1.5 mL of 5.7 M cesium chloride solution placed in an ultracentrifugation tube, the contents were centrifuged for 20 hours at 155,000×g, the supernatant was then discarded, and the RNA precipitate was recovered. The precipitate was dissolved in 3 mL of 10 mM Tris-HCl, 1 mM EDTA-2Na, pH 8.0 (referred to as TE buffer), an equivalent amount of phenol:chloroform:isoamyl alcohol (volumetric ratio of 25:24:1) was furthermore added, the ingredients were mixed and then centrifuged, and the upper aqueous layer was recovered. 1/10-fold 3 M sodium acetate (adjusted to pH 6.2 with glacial acetic acid) and 2.5-fold ethanol were added to the aqueous layer, the ingredients were mixed, and the mixture was allowed to stand over night at −20° C. The mixture was then centrifuged for 20 minutes at 17,000×g, and the resulting precipitate was washed with 70% ethanol and dried at reduced pressure.

The dried preparation was dissolved in 500 μL of the aforementioned TE buffer, giving total RNA solution. The RNA solution was incubated for 5 minutes at 65° C. and then quenched on ice. An equivalent amount of 2×binding buffer (10 mM Tris-HCl, 5 mM EDTA-2Na, 1 M NaCl, 0.5% SDS, pH 7.5) was added to the RNA solution, and the solution was layered on an oligo dT cellulose column (by Clontech) equilibrated with equilibration buffer (10 mM Tris-HCl, 5 mM EDTA-2Na, 0.5 M NaCl, 0.5% SDS, pH 7.5). The column was then flushed with about 10-fold equilibration buffer described above, and the poly (A) $^+$RNA was eluted with elution buffer (10 mM Tris-HCl, 5 mM EDTA-2Na, pH 7.5).

1/10-fold 3 M sodium acetate aqueous solution described above and 2.5-fold ethanol were added to the resulting eluate, the ingredients were mixed, and the mixture was allowed to stand at −70° C. The mixture was then centrifuged for 20 minutes at 10,000×g, and the resulting precipitate was washed with 70% ethanol and dried at reduced pressure. The dried preparation was again dissolved in 500 μL TE buffer and repeatedly purified on an oligo dT cellulose column. The resulting poly (A) $^+$RNA from the roots of the low temperature treated *Cucurbita ficifolia* Bouche was used to prepare a cDNA library for PCR and a cDNA library for isolating the full-length gene.

(2) Preparation of cDNA Library for Low Temperature PCR

The cDNA library was prepared using a Marathon cDNA Amplification Kit (by Clontech). The poly (A) $^+$RNA from the roots of the *Cucurbita ficifolia* Bouche obtained in (1) was used as template, and reverse transcriptase and modified lock-docking oligo(dT) primer with two degenerate nucleotide positions at the 3' end were used to synthesize double-stranded cDNA according to the method of Gubler, Hoffman, et al (Gene, 25, 263-269 (1983)).

A Marathon cDNA adapter (the 5' end phosphorylated to facilitate binding to both ends of the ds cDNA with T4 DNA ligase) was ligated to both ends of the resulting cDNA. The resulting adapter-linked cDNA was used as a *Cucurbita ficifolia* Bouche root-derived PCR cDNA library.

(3) Design of PCR Primers

The base sequences of arginine decarboxylase, S-adenosylmethionine decarboxylase, and spermidine synthase genes already isolated from plants or mammals were compared. Regions with extremely highly conserved homology were selected to synthesize DNA oligomers (sequence primers I through VI).

```
SPDS primer I:                  (SEQ ID NO. 7)
5'-GTTTTGGATGGAGTGATTCA-3'

SPDS primer II:                 (SEQ ID NO. 8)
5'-GTGAATCTCAGCGTTGTA-3'

SAMDC primer III:               (SEQ ID NO. 9)
5'-TATGTGCTGTCTGAGTCGAGC-3'

SAMDC primer IV:                (SEQ ID NO. 10)
5'-GCTAAACCCATCTTCAGGGGT-3'

ADC primer V:                   (SEQ ID NO. 11)
5'-GGGCT(T/G)GGA(G/A)T(G/C)GACTA(C/T)-3'

ADC primer VI:                  (SEQ ID NO. 12)
5'-(T/C)CC(A/G)TC(A/G)CTGTC(G/A)CA(G/C)GT-3'
```

(4) Amplification by PCR

The cDNA library for PCR obtained in (2) was used as template, and the sequence primers designed in (3) were used for PCR. The PCR steps involved 5 cycles of 30 seconds at 94° C., 1 minute at 45° C., and 2<minutes at 72° C., followed by 30 cycles of 30 seconds at 94° C., 1 minute at 55° C., and 2 minutes at 72° C.

(5) Agarose Gel Electrophoresis

Electrophoresis of the PCR amplified products on 1.5% agarose was followed by ethidium bromide staining of the electrophoresed gel and detection of amplified bands on a UV transilluminator.

(6) Verification and Recovery of PCR Amplified Products

The detected amplified bands were verified and were cut out of the agarose gel with a razor. The pieces of gel were transferred to 1.5 mL microtubes, and the DNA fragments were isolated and purified from the gel using a QIAEX II Gel Extraction Kit (by QIAGEN). The recovered DNA fragments were subcloned to the pGEMT cloning vector (by Promega), transformed with *E. coli*, and then used to prepare plasmid DNA in the usual manner.

(7) Sequencing

The sequencing of the sequences inserted into the plasmids were determined by the dideoxy method (Messing, Methods in Enzymol., 101, 20-78 (1983)). Three types of SPDS gene, one type of SAMDC gene, and two types of ADC gene were isolated.

(8) Detection of Homology

A homology search of the base sequences of these genes against a database of known gene base sequences revealed that the SPDS genes had 70% homology with known plant-derived SPDS genes, that the SAMDC gene had at least 70% homology with known plant-derived SAMDC genes, and that the ADC genes had at least 67% homology with known plant-derived ADC genes.

(9) Northern Blotting

Northern blotting was performed in the following manner to ensure that the expression of these genes changed when exposed to cold stress in root tissue exhibiting cold stress resistance.

RNA was extracted from the roots, stems, and leaves of *Cucurbita ficifolia* Bouche which had undergone 6 days of cold stress treatment at 14° C. and roots, stems, and leaves of *Cucurbita ficifolia* Bouche which had undergone 6 days of optimal temperature treatment at 23° C. The RNA was extracted in the manner given in Example 2. Electrophoresis of 10 µg of the resulting RNA on 1.5% formaldehyde agarose gel was followed by blotting overnight on HyBond N nylon membranes. The RNA was fixed with a UV crosslinker and then pre-hybridized for 2 hours at 42° C. in pre-hybridization buffer (50% formamide, 5×SSPE, 5× Denhardt's, 0.1% SDS, 80 µg/mL salmon sperm DNA, pH 7.0). Probes were prepared with the use of $^{32}$P-dCTP and a random label kit (by Amersham) from the 6 types of cDNA obtained by PCR. The probe was added to the pre-hybridization mixture for hybridization over night at 42° C. After the hybridization, the membranes were washed twice for 30 minutes at 50° C., beginning with a washing solution containing 2×SSC and 0.1% SDS, and ending with a washing solution containing 0.1×SSC and 0.1% SDS. Autoradiographs of the membranes were taken using X-ray film (by Kodak).

Figure 5:
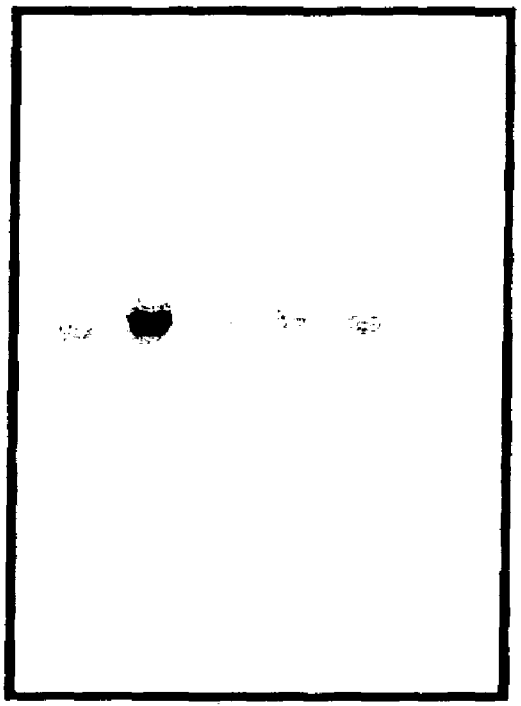
FIG. 5 illustrates the results of expression of the SPDS gene in various types of tissue of *Cucurbita ficifolia* Bouche.
Figure 6:
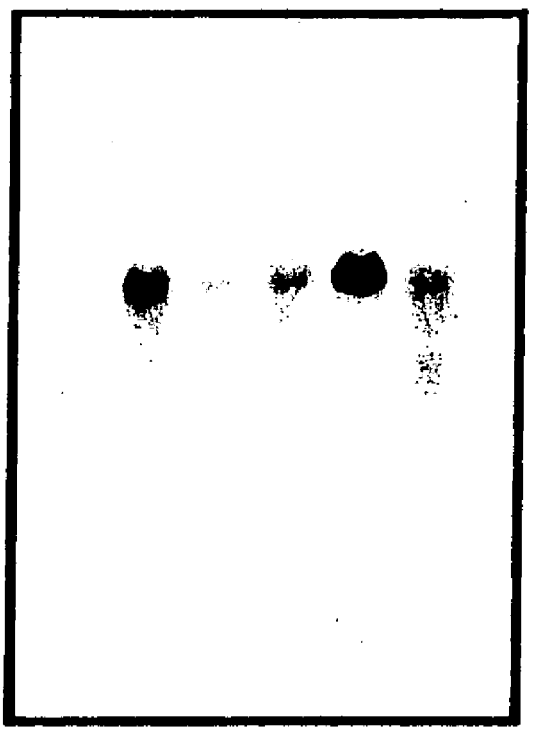
FIG. 6 illustrates the results of expression of the SAMDC gene in various types of tissue of *Cucurbita ficifolia* Bouche.
Figure 7:
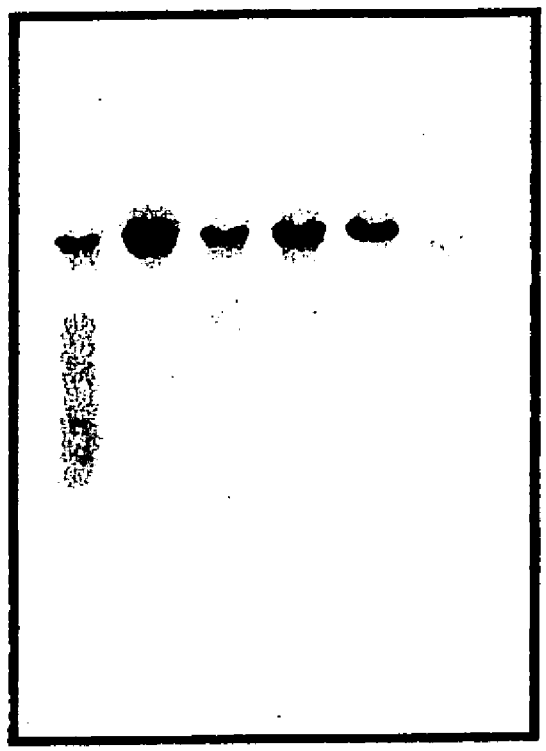
FIG. 7 illustrates the results of expression of the ADC gene in various types of tissue of *Cucurbita ficifolia* Bouche.

The results of Northern blotting are given in FIGS. 5, 6, and 7.

The results in FIG. 5 show that the level of the expression of the SPDS genes which had been obtained was greater when exposed to 14° C. cold stress in highly cold stress-resistant root tissue, and that the level of expression of the SPDS genes was not significantly greater as a result of 14° C. cold stress in stems and leaf tissue with poor cold stress resistance.

The results of FIG. 6 show that the level of the expression of the SAMDC gene which had been obtained was greater when exposed to 14° C. cold stress in highly cold stress-resistant root tissue, and that the level of expression of the SAMDC gene was not significantly greater as a result of 14° C. cold stress in stems and leaf tissue with poor cold stress resistance.

The results of FIG. 7 show that the, level of the expression of the ADC genes which had been obtained was greater when exposed to 14° C. cold stress in highly cold stress-resistant root tissue, and that the level of expression of the ADC genes was not significantly greater as a result of 14° C. cold stress in stems and leaf tissue with poor cold stress resistance.

Based on the above results, it was concluded that the three aforementioned types of polyamine metabolism-related enzyme genes were characterized by higher levels of expression specific to cold stress in the root tissue of highly cold stress-resistant *Cucurbita ficifolia* Bouche, and were genes intimately involved in cold stress resistance. These results and the results of Example 1 suggest that the level of the expression of specific polyamine metabolism-related enzyme genes such as the SPDS, SAMDC, and ADC genes increase in the roots of *Cucurbita ficifolia* Bouche when exposed to cold stress, thereby activating polyamine metabolism and resulting in a greater content of polyamines such as spermidine and spermine. It can thus be concluded that the increase in polyamine content during exposure to cold stress can increase the resistance of roots to cold stress. The three aforementioned polyamine metabolism-related enzyme genes are genes involved in cold stress resistance.

(10) Obtaining Full-Length Genes

Full-length genes were obtained by plaque hybridization. cDNA libraries were prepared using the ZAP-cDNA Synthesis Kit (Stratagene). The poly (A) $^+$RNA from the roots of *Cucurbita ficifolia* Bouche obtained in (1) was used as template, and oligo(dT) primers were used to synthesize double-stranded cDNA according to the method of Gubler, Hoffman, et al (Gene, 25, 263-269 (1983)).

EcoRI adapters (with internal XhoI and SpeI sites) were ligated to both ends of the resulting cDNA, which was digested with XhoI, the fragments were ligated to the EcoRI and XhoI sites in the arm of a λ phage vector (λZAPII) and were then packaged using an in vitro packaging kit (Gigapack Gold, by Stratagene), and the *E. coli* SURE strain (OD 660=0.5) was infected, giving numerous recombinant λ phages. These were used as the *Cucurbita ficifolia* Bouche root-derived cDNA library. The library size was $8.0 \times 10^6$.

To prepare probe, the insert cDNA was isolated and purified from the plasmid DNA of the SPDS, SAMDC, and ADC genes prepared in (6), the resulting cDNA was used as template, and a Random Primed DNA Labeling Kit (USB) was used to prepare $^{32}$P labeled probe. The resulting $^{32}$P labeled cDNA was used as probe.

The phages used to construct the *Cucurbita ficifolia* Bouche root-derived cDNA library were used to infect *E. coli* for amplification on LB agar medium, and about 50,000 copies of phage DNA were photographed on nylon membranes (HyBond-N, by Pharmacia).

The nylon membranes on which the phage DNA was photographed were transferred onto filter paper containing alkali denaturation solution (0.5 M NaOH, 1.5 M NaCl), the membranes were allowed to stand for 4 minutes, and they were then transferred onto filter paper containing neutralization solution (0.5 M Tris-HCl, 1.5 M NaCl, pH 8.0) and allowed to stand for 5 minutes. The membranes were washed with 2×SSC (0.3 M NaCl, 0.03 M trisodium citrate), and the DNA was then fixed on the membranes using Stratalinker (by Stratagene). The nylon membranes on which the DNA had been fixed were placed in hybridization solution (50% formamide, 0.5% SDS, 6×SSPE (3 M NaCl, 0.2 M NaH$_2$PO$_4$, 20 mM EDTA-2Na, pH 7.4), 5× Denhardt's solution (0.1% Ficoll, 0.1% polyvinyl pyrrolidone, 0.1% bovine serum albumin), 50 µg/mL denatured salmon sperm DNA) to bring about pre-hybridization for 3 hours at 42° C., the cDNA probe that had been prepared was added, and hybridization was brought about for 18 hours at 42° C. The membranes were then taken out and washed for 1 to 2 hours at 42° C. with solution containing 2×SSC, 1×SSC, 0.5×SSC, and 0.1×SSC. The membranes were dried and were then placed on X-ray film and exposed over night.

Positive clones hybridized with probe obtained from the SPDS, SAMDS, and ADC gene fragments could thus be selected.

Plasmid clones with cDNA inserts were prepared by in vivo excision from the phage DNA of the positive clones. The in vivo excision followed the method in the ZAP-cDNA Synthesis Kit (Stratagene).

200 µL phage solution containing the SPDS, SAMDC, and ADC genes, 200 µL *E. coli* XL1-Blue suspension, and 1 µL of helper phage R408 suspension were mixed, the mixtures were incubated for 15 minutes at 37° C., 3 mL of 2×YT medium was added for 2 hours of shaking culture at 37° C., the cultures were treated for 20 minutes at 70° C. and centrifuged (10 minutes at 4,000×g), and the supernatant was recovered. 30 µL of the resulting supernatant and 30 µL *E. coli* SURE suspension were mixed, the mixture was incubated for 15 minutes at 37° C., and several µL was used to inoculate LB agar medium containing 50 ppm ampicillin for culture over night at 37° C. The *E. coli* forming colonies contained plasmids with cDNA inserts. The base sequences of the inserted sequences in the plasmids were sequenced by the dideoxy method (Messing, Methods in Enzymol., 101, 20-78 (1983)). The results showed that the plasmids contained start codons.

The resulting full-length spermidine synthase genes from *Cucurbita ficifolia* Bouche were designated FSPD1 (SEQ ID NOS. 1 and 2), the S-adenosylmethionine decarboxylase gene was designated FSAM24 (SEQ ID NOS. 3 and 4), and the arginine decarboxylase gene was designated FADC76 (SEQ ID NOS. 5 and 6).

The amino acids of the resulting FSPD1 were compared with those of known plant-derived spermidine synthase genes (Table 1). The results of Table 1 show that FSPD1 from *Cucurbita ficifolia* Bouche roots had high homology at the amino acid level with other plant-derived SPDS genes.

TABLE 1

Comparison of *Cucurbita ficifolia* Bouche FSPD1 gene and other SPDS genes

| Plant | Origin | Amino acid homology (%) |
|---|---|---|
| Arabidopsis thaliana | | 83.8 |
| Nicotiana sylvestris | Leaves | 82.1 |
| Hyoscyamus niger | roots | 86.5 |

The amino acids of the resulting FSAM24 were compared with those of known plant-derived S-adenosylmethionine decarboxylase genes (Table 2). The results of Table 2 show that FSAM24 from *Cucurbita ficifolia* Bouche roots had high homology at the amino acid level with other plant-derived SAMDC genes.

TABLE 2

Comparison of *Cucurbita ficifolia* Bouche FSAM24 gene and other SAMDC genes

| Plant | Origin | Amino acid homology (%) |
|---|---|---|
| Arabisopsis thaliana | | 66.3 |
| Spinacia oleracea | seedlings | 63.3 |
| Solanum tuberosum | | 68.2 |
| Pisum sativum | undifferentiated-calli | 65.2 |

The amino acids of the resulting FADC76 were compared with those of known plant-derived arginine decarboxylase genes (Table 3). The results of Table 3 show that FADC76 from *Cucurbita ficifolia* Bouche roots had high homology at the amino acid level with other plant-derived ADC genes.

TABLE 3

Comparison of *Curcurbita ficifolia* Bouche FADC76 gene and other ADC genes

| Plant | Origin | Amino acid homology (%) |
|---|---|---|
| Lycopersicon esculentum | fruit | 77.1 |
| Nicotiana sylvestris | | 75.4 |
| Arabidopsis thaliana | | 70.7 |
| Pisum sativum | fruit | 70.6 |

EXAMPLE 3

Preparation of Transgenic *Arabidopsis thaliana*

(1) Preparation of Expression Construct

Figure 8:
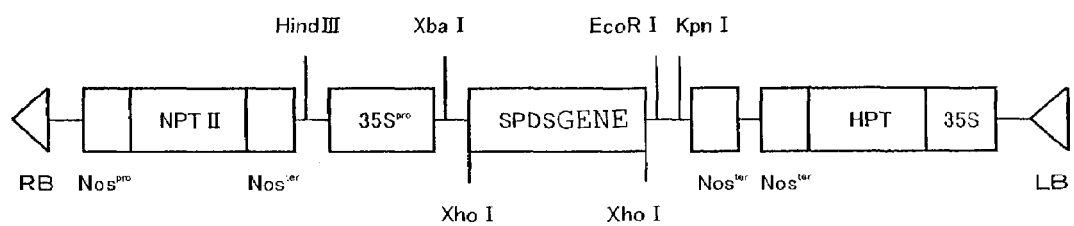
FIG. 8 illustrates the structure of two expression constructs containing a polyamine metabolism-related gene: Part 1 is the SP DS(+)(−) Hm2 is construct, and part 2 is the SPDS(−)(−) Hm2 construct.
Figure 8:
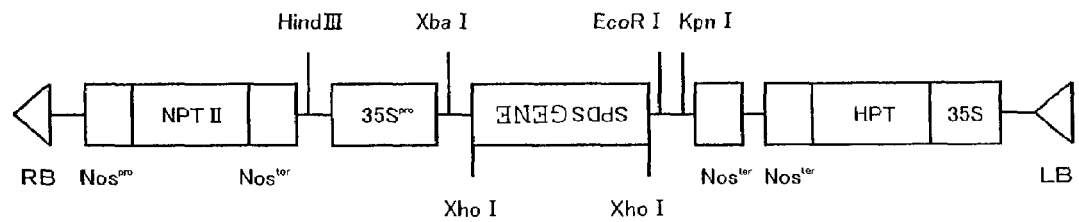

The FSPD1 polyamine metabolism-related gene given in SEQ ID NO. 1 was cleaved with XhoI in such a way that the entire reading frame of the base sequence was included, and the fragment was purified by the glass milk method. pGEM-7Zf (Promega) was then cleaved with XhoI, and the FSPD1 fragments were subcloned in the sense and antisense directions. The FSPD1 fragments were again cleaved with the XbaI and KpnI restriction enzymes at the multicloning site of pGEM-7Zf, and were subcloned in the sense and antisense direction to the binary vector pBI101-Hm2 to which the 35S promoter had been ligated. The resulting plasmid was designated pBI35S-FSPD1. The structure of this expression construct is given in FIG. 8. Transformed *E. coli* JM109 was designated *Escherichia coli* JM109/pBI35S-FSPD1.

The polyamine metabolism-related gene FSAM24 given in SEQ ID NO. 3 was cleaved with NotI in such a way that the entire reading frame of the base sequence was included, and the ends were blunted. The fragments were subcloned to the binary vector pBI101-Hm2 to which the (blunted) 35S promoter had been ligated. The resulting plasmid was designated pBI35S-FSAM24. Transformed *E. coli* JM109 was designated *Escherichia coli* JM109/pBI35S-FSAM24.

The polyamine metabolism-related gene FADC76 given in SEQ ID NO. 5 was cleaved with NotI in such a way that the entire reading frame of the base sequence was included, and the ends were blunted. The fragments were subcloned to the binary vector pBI101-Hm2 to which the (blunted) 35S promoter had been ligated. The resulting plasmid was designated pBI35S-FADC76. Transformed *E. coli* JM109 was designated *Escherichia coli* JM109/pBI35S-FADC76.

(2) Introduction of Plasmids to *Agrobacterium*

The *E. coli* pBI35S-FSPD1, *E. coli* pBI35S-FSAM24, or *E. coli* pBI35S-FADC76 obtained in (1) and the *E. coli* strain with the pRK2013 helper plasmid were cultured for 1 night at 37° C. on LB medium containing 50 mg/L kanamycin, and the *Agrobacterium C*58 strain was cultured for 2 nights at 37° C. on LB medium containing 50 mg/L kanamycin. Cells were harvested from 1.5 mL of each culture in Eppendorf tubes and then washed with LB medium. The cells were suspended in 1 mL of LB medium, 100 µL each of the three types of cells were mixed to inoculate LB agar medium and cultured at 28° C. to allow the plasmids to be conjugated with the *Agrobacterium* (tripartite conjugation). After 1 or 2 days, portions were scraped with a platinum loop and smeared on LB agar medium containing 50 mg/L kanamycin, 20 mg/L hygromycin, and 25 mg/L chloramphenicol. After 2 days of culture at 28° C., a variety of single colonies were selected. The resulting transformants were designated C58/pBI35S-FSPD1, C58/pBI35S-FSAM24, and C58/pBI35S-FADC76. Transgenic *Arabidopsis thaliana* was prepared by reduced pressure infiltration ((3) through (6) below) or callus regeneration ((7) through (12) below).

(3) Cultivation of *Arabidopsis thaliana*

Potting compost METROMIX® (Hyponex Japan) was placed in plastic pots, the surfaces were covered with netting mesh, and 2 to 5 seeds (donated by Professor Takayuki Kawauchi of Nara Institute of Science and Technology Graduate University) of *Arabidopsis thaliana* (referred to below as the "Columbia strain" or "wild type") were inoculated through the interstices of the mesh. The pots were placed for 2 days at 4° C. in a low temperature chamber to germinate, and were then transferred for cultivation under 22° C. long-day conditions (16 hour long day/8 hour night). After about 4 to 6 weeks, lateral shoots were induced by top pruning plants in which the main axis flower stalk was extended to between 5 and 10 cm. After about 1 to 2 weeks of top pruning, the plants were infected with *Agrobacterium*.

(4) Preparation of *Agrobacterium* Suspension 2 days before infection, the *Agrobacterium* prepared in (2) above was used to inoculate 10 mL LB medium containing antibiotics (50 μg/mL kanamycin, 20 μg/mL hygromycin) for 24 hours of shaking culture at 28° C. Portions of the culture were transferred to 1000 mL LB medium containing antibiotics (50 μg/mL kanamycin, 20 μg/mL hygromycin) for about another 24 hours of shaking culture at 28° C. (to an $OD_{600}$ of between 1.2 and 1.5). Cells were harvested from the culture at ambient temperature and were resuspended in suspension medium for infiltration (0.5×MS salt, 0.5×Gamborg B5 vitamin, 1% sucrose, 0.5 g/L MES, 0.44 μM benzylaminopurine, 0.02% Silwet-77) to an $OD_{600}$ of between 0.8 and 1.

(5) *Agrobacterium* Infection

The potting soil in the pots of *Arabidopsis thaliana* prepared in (3) above was watered to prevent the potting soil from absorbing the *Agrobacterium* suspension prepared in (4) above. Approximately 200 to 300 mL of the *Agrobacterium* suspension was placed in 1000 mL beakers, and the potted *Arabidopsis thaliana* was turned upside down to dip the plants in the suspension. The beakers in which the pots had been placed were put into a dessicator, which was suctioned with a vacuum pump to about −0.053 MPa (400 mmHg), and the plants were then allowed to stand for about 10 minutes. The negative pressure was gradually released, the plants were then taken out of the *Agrobacterium* suspension, the excess *Agrobacterium* suspension was wiped off with a Kimtowel, and the pots were placed on their sides in deep-bottomed trays. A small amount of water was introduced, and the plants were covered with saran wrap. The plants were allowed to stand in this manner for about 1 day. The saran wrap was then removed, and the pots were placed upright and irrigation was stopped for about 1 week. The potting compost was then gradually watered, and seeds were harvested from matured pods for about 3 to 5 weeks. The harvested seeds were strained through a tea strainer to eliminate debris and husks, and the seeds were placed in a dessicator and thoroughly dried.

(6) Obtaining Transformed Plants

100 μL (about 2000) seeds obtained in (5) above were transferred to 1.5 mL Eppendorf tubes and soaked for 2 minutes in 70% ethanol and 15 minutes in 5% sodium hypochlorite solution, and the seeds were finally washed five times with sterile water to disinfect the seeds. The disinfected seeds were transferred to 15 mL falcon tubes, about 9 mL of 0.1% aseptic agar solution was added, and the contents were vigorously mixed. A 0.1% agar mixture of seeds was evenly spread on selection medium (1×MS salt, 1×Gamborg B5 vitamin, 1% sucrose, 0.5 g/L MES, 0.8% agar, 100 mg/L carbenicillin, 50 mg/L kanamycin, 40 mg/L hygromycin, 8 g/L Phytagar, pH 5.7) like plating the phages. The plates were dried for about 30 minutes in a clean bench, a 4° C. low temperature treatment was performed for 2 days, the plates were transferred to a 22° C. growth chamber, and transformants with antibiotic resistance were selected. Plants with about 3 to 5 true leaves were again transferred to fresh selection medium and cultivated until 4 to 6 true leaves had grown. Transformants with antibiotic resistance (T1) were planted in pots filled with compost and acclimated under humid conditions for about 5 to 7 days. After acclimation, the plants were cultivated at 23° C. under long day conditions (16 hour long days/8 hour nights). The resulting transformed plants (T1) and plants T2 grown from seeds (T2) obtained from the transformed plants were analyzed for genes introduced by PCR or Southern hybridization and their levels of expression by Northern hybridization were analyzed, so as to confirm that the target polyamine metabolism-related enzyme genes had been incorporated in a consistent manner and that transformants had been expressed. Seeds T3 were also harvested from the plants T2, and antibiotic resistance tests (segregation analysis) were conducted to obtain homozygotes (T2) based on the proportion in which transformants appeared. Seeds T2 and seeds T3 obtained from the homozygotes (T3 homozygous cell line) were used in the following tests.

(7) Aseptic *Arabidopsis thaliana* Cultivation 10 seeds (donated by Professor Atsuhiko Shinmyo of Nara Institute of Science and Technology Graduate University) of the *Arabidopsis thaliana* Wassilewskija strain (referred to below as the WS strain) were introduced into 1.5 mL tubes, 1 mL of 70% ethanol was added, and the seeds were allowed to stand for 3 minutes. The seeds were then dipped for 3 minutes in disinfecting solution (5% sodium hypochlorite, 0.02% Triton X-100), washed 5 times with sterilized water, and then planted in MSO plates (4.6 g Murashige-Skoog mineral salts, 10 g sucrose, 1 mL/L 1000× vitamin stock, pH 6.2). The plates were allowed to stand for 2 days at 4° C. to carry out low temperature treatment, and they were then cultured for 21 days in plant incubators (MLR-350HT, by Sanyo) under conditions involving long days (16 hour long days, 8 hour nights) at 22° C. and a light intensity of 6000 lux. To improve the infection efficiency, the plants were again aseptically plucked out, the roots were spread out on the surface of fresh MSO plates; and the culture was continued for another 2 days.

(8) *Agrobacterium* Infection

Several roots of the WS strain cultured for 21 days above were arranged and cut with a scalpel to between about 1.5 and 2.0 cm, and they were placed alongside each other on CIM plates (MSO plates supplemented with 2,4-dichlorophenoxyacetic acid to a final concentration of 0.5 μg/mL and kinetin to a final concentration of 0.05 μg/mL). Samples which had been cultured for 2 days at a light intensity of 3000 lux in 16 hours of light/8 hours of darkness and diluted 3-fold with MS dilution solution (6.4 g/L Murashige-Skoog mineral salts, pH 6.3) were aliquoted in 1 mL portions to tubes, and slices of the roots on which callus was forming were dipped for 10 minutes in the tubes. The slices were placed on doubled disinfected filter paper, the excess moisture was removed, and the slices were arranged on fresh CIM plates for two days of co-cultivation under the same conditions.

(9) Disinfection

Slices on which the strains had grown enough to become visible to the naked eye were transferred to a disinfection solution (MS diluting solution supplemented with claforan to a final concentration of 200 μg/mL) and gently shaken to wash them for 60 minutes. These operations were repeated 5 times, the moisture was removed on sterilized filter paper, and the slices were placed on SIMC plates (MSO plates supplemented with 2-ip to a final concentration of 5 μg/mL, IAA to a final concentration of 0.15 μg/mL, and claforan to a final concentration of 500 μg/mL) for 2 days of culture at a light intensity of 6000 lux in 16 hours of light/8 hours of darkness.

(10) Selection of Transformants

The slices cultured for 2 days above were transferred to SIMCS plates (SIMC plates supplemented with hygromycin B to a final concentration of 4.6 U/mL) for culture at a light intensity of 6000 lux in 16 hours of light/8 hours of darkness. The slices were subsequently transferred to fresh SIMCS plates every week. The transformed slices continued to be grown, forming dome-shaped callus, but slices that had not been transformed turned brown. After about 2 weeks, the callus of the transformants turned green. After about 1 month, leaves formed, and after that rosettes formed.

(11) Regeneration of Transformants

The roots of plants with rosette leaves were cut with a knife or scalpel to leave out the callus and were inserted so as to ride gently on RIM plates. After 8 to 10 days, those on which several roots of about 1 to 2 cm had formed were planted using tweezers and cultivated in rock wool minipots (by Nitto Boseki) soaked with mineral salt medium (5 mM $KNO_3$, 2.5 mM K-phosphate buffer (pH 5.5), 2 mM $MgSO_4$, 2 mM $Ca(NO_3)_2$, 50 μM Fe-EDTA, 1000×microelements (70 mM $H_3BO_3$, 14 mM $MnCl_2$, 0.5 mM $CuSO_4$, 1 mM $ZnSO_4$, 0.2 mM $NaMoO_4$, 10 mM NaCl, 0.01 mM $CoCl_2$) 1 mL/L). After flowering and the formation of pods, the plants were transplanted to soil prepared by mixing pearlite and vermiculite (by TES) in a 1:1 ratio, and then soaked with mineral salt media. After about 1 month, several hundred seeds of each strain were obtained. These were subsequently called T2 seeds.

(12) Obtaining Antibiotic Resistant Strains

About 100 T2 seeds were sterilized in the same manner as in (7) and used to inoculate MSH plates. Hygromycin B-resistant strains germinated in a proportion of about 3:1.

(13) DNA Extraction and Southern Hybridization

The germinated T2 seeds above were transplanted using tweezers to rock wool minipots soaked with mineral salts and cultured at a light intensity of 6000 lux and a temperature of 22° C. in 16 hours of light and 8 hours of darkness. After 2 weeks, the top soil was cut away with a scalpel to allow the surface of the rock wool to be stroked with a knife, and samples were immediately frozen with liquid nitrogen. The samples were finely milled in a mortar and pestle in the presence of liquid nitrogen, 3 mL of DNA extraction buffer (200 mM Tris-HCl (pH 8.0), 100 mM EDTA-2Na, 1% N-lauroylsarcosine sodium, 100 μg/mL proteinase K) was added per gram, and the ingredients were thoroughly mixed. The mixture was incubated for 1 hour at 60° C. and then centrifuged (10 minutes at 10,000×g), and the supernatant was filtered through mira cloth and transferred to a fresh tube. It was extracted three times with phenol:chloroform: isoamyl alcohol (25:24:1) and then precipitated in ethanol. The precipitate was dissolved in TE buffer. 20 μg each of genomic DNA was obtained from about 2.0 g of each of the plants. 1 μg of DNA was cleaved with the EcoRI and HindIII restriction enzymes for 1% agarose electrophoresis and Southern hybridization.

Seeds of untransformed WS strain were germinated and allowed to grow, DNA was similarly extracted from the plants and digested with the EcoRI and HindIII restriction enzymes for 1% agarose electrophoresis and Southern hybridization. FSPD1, FSAM24, and FADC76 gene fragments were used as hybridization probes.

Southern hybridization was performed according to the method in *Molecular Cloning, a Laboratory Manual* (Chapter 9, pp. 31-58 (Cold Spring Harbor (1989))). Specifically, electrophoresis of the DNA material on 1% agarose gel was followed by alkali denaturation and Southern blotting overnight on nylon membranes (HyBond-N, by Amersham). The DNA was fixed by 3 minutes of irradiation with a UV transilluminator (254 nm). The membranes were pre-hybridized for 2 hours at 50° C. in 5 mL of pre-hybridization buffer (5× Denhardt's, 6×SSC, 0.1% SDS, 10 μg/mL salmon sperm DNA). Probes were added for hybridization over night at 50° C. After the hybridization, the membranes were washed twice for 10 minutes with washing solution containing 2×SSC and 0.1% SDS, and were then washed twice for 30 minutes at 50° C. with the same solution. The membranes were dried and exposed over night at −80° C. in cassettes filled with X-ray film (by Kodak) to take autoradiographs. The patterns of the signals detected by Southern hybridization were compared for untransformed strains (1), transformants containing FSPD1, FSAM24, and FADC76 (2), and transformants containing only the vector (3).

In addition to the endogenous signal shared in common by (1), (2), and (3), specific signals were observed in EcoRI digests and HindIII digests of (2), confirming that the target gene had been incorporated in (2).

EXAMPLE 4

Northern Blotting Analysis

In order to ascertain whether the target gene was actually expressed in the T2 transformants obtained in Example 3, Northern blotting was performed in the following manner.

Total RNA was extracted from untransformed wild type (WT) and T2 transformant (cell lines: TSP-14, 15, 16, 17, 19) rosette leaves. The RNA was extracted in the same manner as in Example 2. 10 μg of the resulting total RNA was electrophoresed on 1.5% formaldehyde agarose gel and blotted over night on HyBond N nylon membranes. The RNA was fixed with a UV crosslinker and then pre-hybridized for 2 hours at 42° C. in pre-hybridization buffer (50% formamide, 5×SSPE, 5× Denhardt's, 0.1% SDS, 80 μg/mL salmon sperm DNA, pH 7.0). Probes were prepared with the use of $^{32}$P-dCTP and a random label kit (by Amersham) from the cDNA of the transformed *Cucurbita ficifolia* Bouche SPDS gene fragment. The probe was added to the pre-hybridization mixture for hybridization over night at 42° C. After the hybridization, the membranes were washed twice for 30 minutes at 55° C., beginning with a washing solution containing 2×SSC and 0.1% SDS, and ending with a washing solution containing 0.1×SSC and 0.1% SDS. Autoradiographs of the membranes were taken using X-ray film (Kodak).

Figure 9:
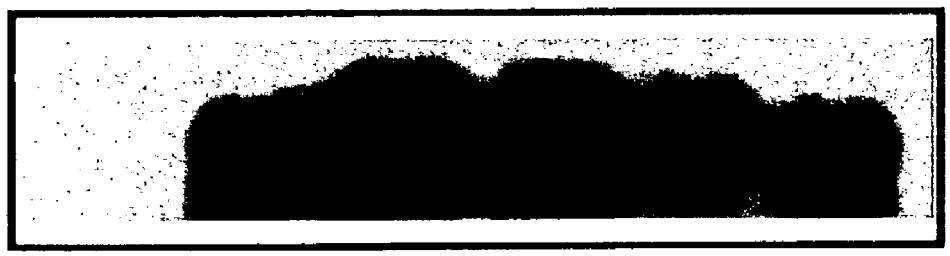
FIG. 9 illustrates the results of expression of the *Cucurbita ficifolia* Bouche SPDS gene in transformants.

The results of Northern blotting are given in FIG. 9. The results in FIG. 9 show that no expression of the exogenous *Cucurbita ficifolia* Bouche SPDS gene was detected in the wild type (WT), but that the *Cucurbita ficifolia* Bouche SPDS gene (FSPD1) was expressed in extremely high levels in all the T2 transformants.

EXAMPLE 5

Evaluation of Polyamine Content (1) Selection of Cell Lines Containing Target Gene Cell lines were selected upon confirmation that the target gene had been introduced by PCR (or Southern analysis) and Northern analysis of the transformants prepared in Example 3, resulting in the selection of cell lines TSP-14, 15, 16, 17, and 19 in which the polyamine metabolism-related enzyme gene had been actually introduced and expressed.

(2) Analysis of Polyamine Content

About 0.05 to 0.2 g of rosette leaves (or true leaves) were sampled from simultaneously cultivated wild type (Columbia) and transformants (TSP), and were transferred to and stored frozen in plastic vials which could be tightly sealed. Diluted internal standards (internal standard amount=2.5 nmol) for assaying putrescine, spermidine, and spermine as well as 5% perchloric acid aqueous solution (4 mL per 1.0 g live weight of sample) were added to the samples, which were thoroughly milled and extracted at ambient temperature in an omnimixer. The resulting solution was centrifuged for 20 minutes at 4° C. and 36,000×g, and the supernatant was recovered. Precisely 1.0 mL of the supernatant was introduced into a centrifugation tube, and precisely 1.0 mL of 12 N HCl was also introduced into the tube, which was tightly sealed and placed in a 110° C. dryer for 18 hours of hydrolysis. The material was concentrated to dryness, precisely 1.0 mL of 5% aqueous perchloric acid was added, and the material was thoroughly lysed. The resulting solution was applied on a cation exchange resin (50 W-4X, 200 to 400 mesh, H+ type, by Biorad) column. The column was flushed with 0.7 N NaCl/0.1 M sodium phosphate buffer (pH 8.0), water, and 1 N hydrochloric acid, in that order, to eliminate organic materials and amino acids other than polyamines. 6 N hydrochloric acid was added to the column, which was drained until no solution came out, and the polyamines were collected. The eluate was concentrated to dryness at 70° C., and 5% perchloric acid was added to dissolve the polyamines. Assay of the content of the polyamines putrescine, spermidine, and spermine involved dansylation followed by analysis with an internal standard using HPLC with a detector. The HPLC column was a μBondapak C18 (027324 by Waters, 3.9×300 mm, 10 μm particle diameter). The polyamine content of the samples was calculated by determining the peak area of the internal standard and each polyamine based on the HPLC chart of the standard solutions and samples. The results are given in Table 4.

TABLE 4

| Cell line | Free polyamine content (nmolg$^{-1}$fw)$^{-1}$ fw) | | | |
|---|---|---|---|---|
| | Putrescine | Spermidine | Spermine | Total polyamines |
| Wild type:WT | 5.41 ± 3.74 | 108.99 ± 12.63 | 11.95 ± 2.92 | 126.35 ± 16.04 |
| TSP-14 | 6.06 ± 3.04 | 149.96 ± 11.64 | 23.68 ± 2.06 | 179.70 ± 20.82 |
| TSP-15 | 8.33 ± 2.05 | 175.76 ± 16.30 | 21.53 ± 1.29 | 205.62 ± 20.82 |
| TSP-16 | 10.66 ± 3.98 | 182.94 ± 23.73 | 21.36 ± 6.48 | 214.96 ± 29.41 |
| TSP-17 | 12.40 ± 3.89 | 177.45 ± 12.70 | 13.33 ± 1.07 | 203.18 ± 16.77 |
| TSP-19 | 7.82 ± 3.55 | 169.13 ± 36.97 | 21.59 ± 3.10 | 198.54 ± 41.49 |

Table 4 shows that cell lines TSP-14, 15, 16, 17, and 19 containing the polyamine metabolism-related enzyme gene had significantly higher levels, particularly of spermidine and spermine, than the wild type (WT), and that the total polyamine content was also significantly higher than in the wild type (WT).

The results showed that the introduction of the polyamine metabolism-related enzyme gene into plants allowed the polyamine content to be controlled through the activation of polyamine metabolism.

EXAMPLE 6

Figure 10:
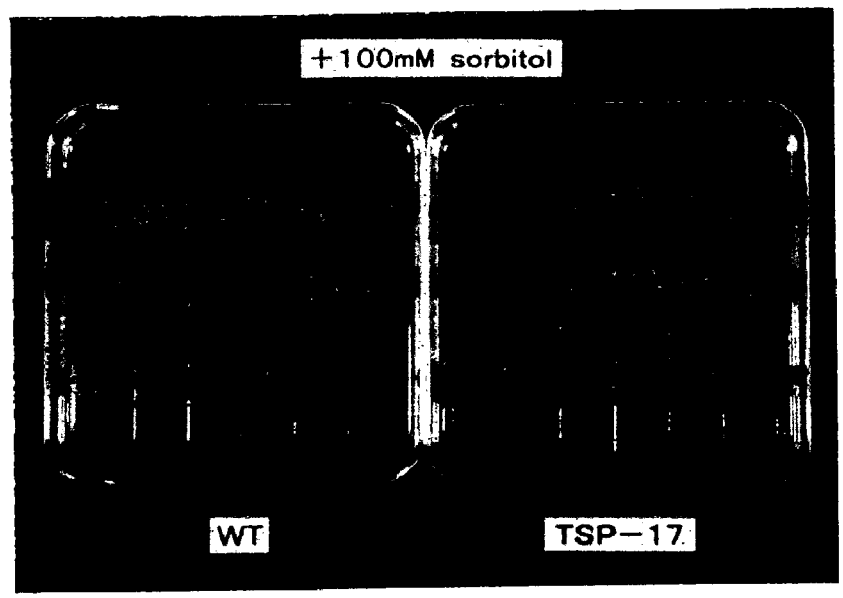
FIG. 10 shows a comparison of osmotic stress damage in plants incorporating the polyamine metabolism-related gene and the wild type.
Figure 10:
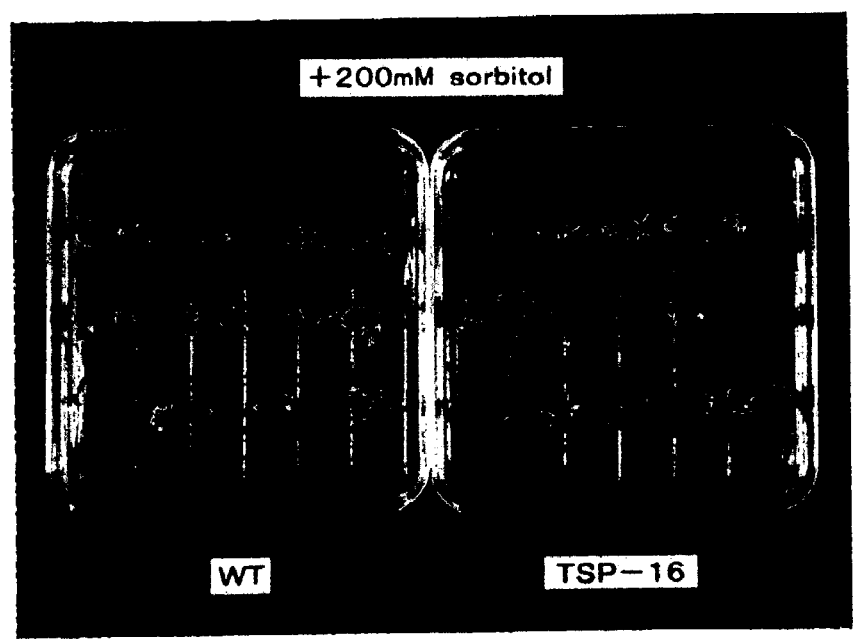

Evaluation of Environmental Stress Tolerance (1) Evaluation of Osmotic Stress Tolerance The surfaces of seeds of the transformants (TSP-15, 16, 17) obtained in Example 3 and the wild type (WT: Columbia strain) were sterilized in the same manner as in section (6) of Example 3. Germination growth media containing 100 mM and 200 mM sorbitol (1×MS salt, 10 g/L sucrose, 0.1 g/L myo-inositol, 5% MES, 8 g/L Phytagar, pH 5.7) was inoculated with the sterilized seeds one at a time. Inoculation was followed by about 2 days of low temperature treatment at 4° C., and then by the start of cultivation at 22° C. under conditions involving long days (16 hour long days/8 hour nights). The state of growth after inoculation was monitored, particularly the state of the growth of plants on germination growth media during weeks 6 and 10. The results are given in FIG. 10.

Several days following inoculation, TSP-15, 16, and 17 showed improved germination than the wild type (WT) on growth medium containing 100 mM and 200 mM sorbitol, revealing improved growth. In week 6 after inoculation, TSP-15, 16, and 17 plants on medium containing 100 mM and 200 mM sorbitol were larger than the WT, with significantly less impaired growth. The results for TSP-17 in particular are given in FIG. 10. After week 7 following inoculation, the plants on TSP-15, 16, and 17 containing 200 mM sorbitol in particular exhibited far improved growth, particularly the roots, compared to WT. In week 10 following inoculation, there were significant differences in both the parts above ground and the roots. The results for TSP-16 in particular are given in FIG. 10. Some of the WT were found to have yellowed and died due to impaired growth.

(2) Evaluation of Drought Stress Tolerance

Two T3 homozygous cell lines were selected from the transformants (TSP-16, etc.) in Example 3. Plastic pots filled with METROMIX® potting compost (Hyponex Japan) were inoculated with seeds of the two T3 homozygous transformants and the wild type (WT: Columbia strain). Inoculation was followed by about 2 days of low temperature treatment at 4° C., and the pots were then placed in plastic vats to start cultivation at 23° C. under conditions involving long days (16 hour long days/8 hour nights). Rosette leaves had fully developed by about week 4 after inoculation. Individuals characterized by uniform growth at the time the rosette leaves had fully developed were selected, water was then fed into the vats to ensure uniform soil moisture, and water was filled to the middle of the plastic pots. After 5 days, a constant soil moisture was confirmed, and drought stress treatment was started (termination of water feed). The state of growth was monitored immediately after water termination.

Figure 11:
FIG. 11 shows a comparison of drought stress damage in plants incorporating the polyamine metabolism-related gene and the wild type.

Withering from drought stress damage was noted in the wild type (WT) on day 13 after the start of drought treatment. 50% of the WT plants had died by Day 14 of drought treatment. By contrast, 20% of the plants of the two T3 homozygous cell lines had died, indicating a higher survival rate than the WT. 100% of the WT had died by day 15 after the start of drought treatment, whereas 30% of the T3 homozygous cell lines had survived. The results are given in FIG. 11. The results of FIG. 11 clearly show that the WT (on left) had died, and that the T3 homozygous cell lines (on right) had survived. All plants of the T3 homozygous cell lines had died by day 17 after the start of treatment. The above results clearly show that the T3 homozygous cell lines had a higher survival rate after the start of the drought treatment compared to the WT, demonstrating improved drought stress tolerance.

(3) Evaluation of Cold Stress Tolerance (Freeze Stress Tolerance)

The surfaces of seeds of the transformants (TSP-16) obtained in Example 3 and the wild type (WT: Columbia strain) were sterilized in the same manner as in section (6) of Example 3. Germination growth media (1×MS salt, 10 g/L sucrose, 0.1 g/L myo-inositol, 5% MES, 5 g/L Gellan gum, pH 5.7) was inoculated with the sterilized seeds one at a time. Inoculation was followed by about 2 days of low temperature treatment at 4° C., and then by the start of cultivation at 22° C. under conditions involving long days (16 hour long days/8 hour nights). In week 4 after inoculation, the germination growth medium was transferred to a low temperature incubator (CR-14 by Hitachi) to start freeze stress treatment. The freeze stress treatment involved 9 hours at 9° C., 24 hours at −6° C., and another 9 hours at 9° C. The plants were then transferred to a 22° C. growth chamber to look for cold stress damage. The results are given in FIG. 12.

Figure 12:
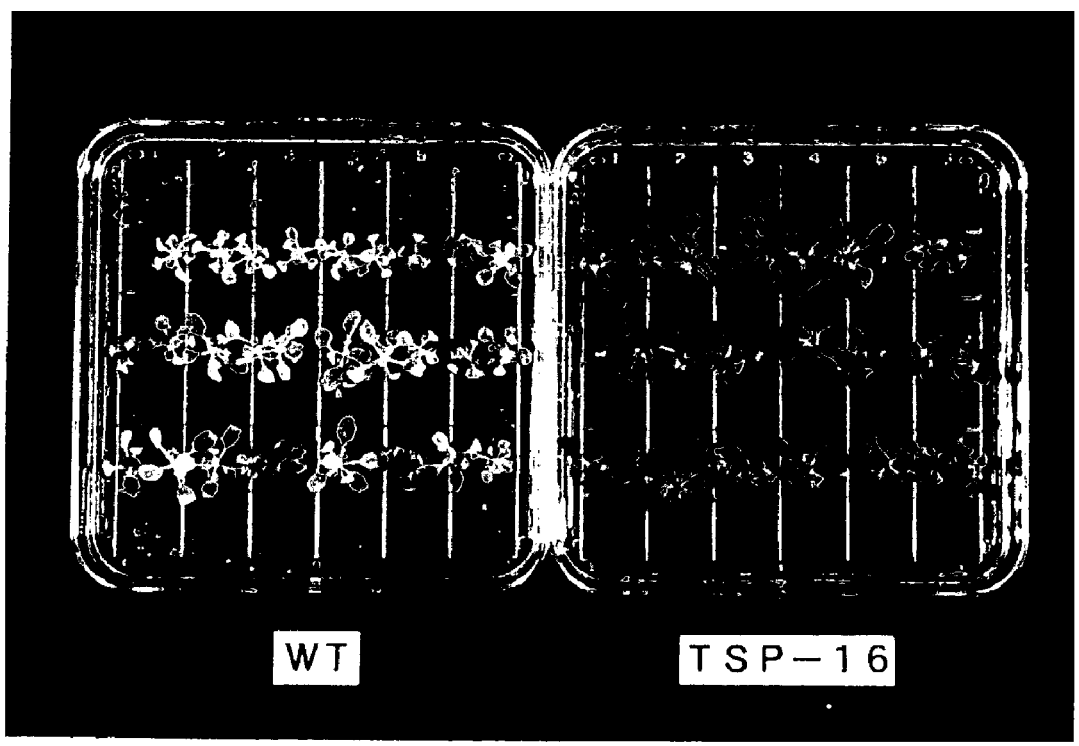
FIG. 12 shows a comparison of cold damage in plants incorporating the polyamine metabolism-related gene and the wild type.

The results in FIG. 12 show that membrane leakage resulting from cold stress damage was found in the WT control, and that 2 days after being transferred to the 22° C. incubator, the leaves turned extremely white (and subsequently died). No membrane leakage was noted in the transformants containing the polyamine metabolism-related enzyme gene, with no whitening of the leaves as a result of cold stress damage. Similar results were obtained in other cell lines containing polyamine metabolism-related enzyme genes.

The above results show that the introduction of polyamine metabolism-related enzyme genes into plants results in plants with significantly improved cold stress resistance.

(4) Evaluation of Salt Stress Tolerance

The surfaces of seeds of the transformants (TSP-16) obtained in Example 3 and the wild type (WT: Columbia strain) were sterilized in the same manner as in section (6) of Example 3. Germination growth medium containing 50 mM NaCl (50 mM NaCl, 1×MS salt, 10 g/L sucrose, 0.1 g/L myo-inositol, 5% MES, 5 g/L Gellan gum, pH 5.7) was inoculated with the sterilized seeds one at a time. Inoculation was followed by about 2 days of low temperature treatment at 4° C., and then by the start of cultivation at 22° C. under conditions involving long days (16 hour long days/8 hour nights). In week 4 after inoculation, the extent of plant growth on the germination growth medium was observed. The results are given in FIG. 13.

Figure 13:
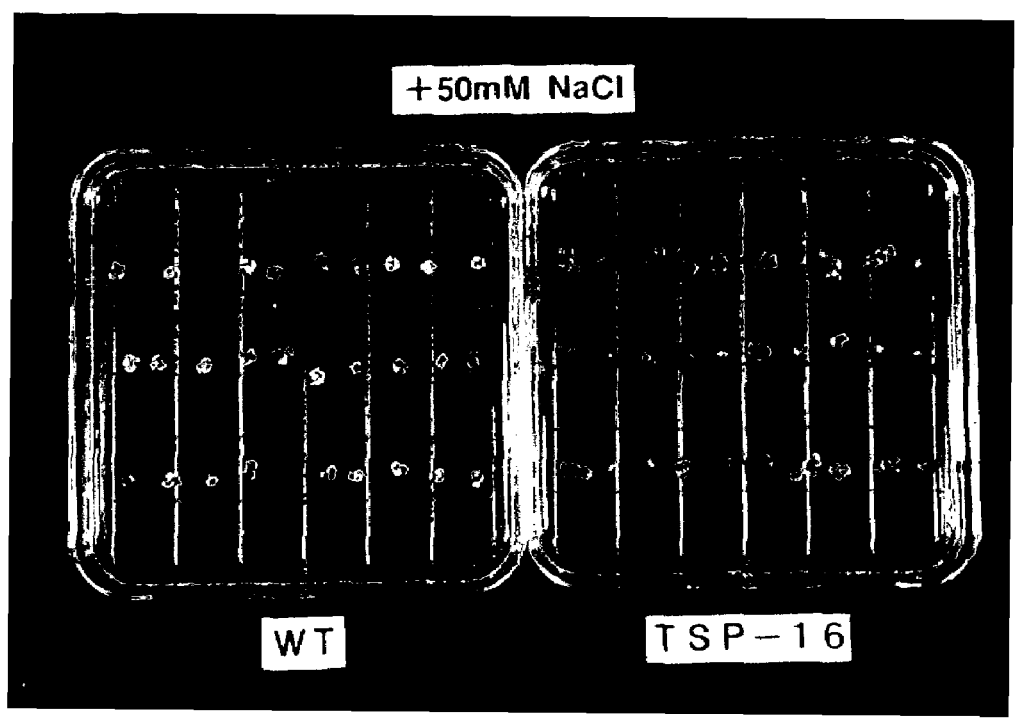
FIG. 13 shows a comparison of salt stress damage in plants incorporating the polyamine metabolism-related gene and the wild type.

The results of FIG. 13 show that the growth of the control WT was seriously impaired on medium containing 50 mM NaCl, and that the plants in their entirety had turned white and died 3 to 4 weeks after inoculation. Although the growth of the transformants containing the polyamine metabolism-related enzyme gene was impaired, true leaves developed, and the plants had not died 3 to 4 weeks after inoculation. Similar results were obtained in other cell lines containing polyamine metabolism-related enzyme genes.

The above results show that the introduction of polyamine metabolism-related enzyme genes to plants result in plants with significantly improved salt stress resistance.

(5) Evaluation of Herbicidal Stress Tolerance

The surfaces of seeds of the transformants obtained in Example 3 (cell lines: pBI121 (35S-GUS), TSP-15, TSP-16; cell lines with the polyamine metabolism-related enzyme gene introduced in the antisense direction: TSP-21, TSP-22) and the wild type (WT: Columbia strain) were sterilized in the same manner as in section (6) of Example 3. Germination growth medium containing 2 µM paraquat (PQ) (2 µM paraquat, 1×MS salt, 10 g/L sucrose, 0.1 g/L myo-inositol, 5% MES, 5 g/L Gellan gum, pH 5.7) was inoculated with the sterilized seeds one at a time. Inoculation was followed by about 2 days of low temperature treatment at 4° C., and then by the start of cultivation at 22° C. under conditions involving long days (16 hour long days/8 hour nights). The number of germinating individuals (germination rate) was observed on day 10 after inoculation, and the number of individuals surviving (survival rate) was observed on day 20. The results are given in Table 5.

TABLE 5

| Cell line | Germination rate | Survival rate |
| --- | --- | --- |
| Wild type:WT | 3% | 3% |
| pBI121:35S-GUS | 0% | 0% |
| TSP-15 | 50% | 25% |
| TSP-16 | 59% | 50% |

The results of Table 5 show that the wild type and vector control line (pBI121) had extremely low germination and survival rates as a result of toxicity caused by paraquat, whereas cell lines TSP-15 and TSP-16 which contained polyamine metabolism-related enzyme genes retained high germination and survival rates.

The above results clearly show that the introduction of polyamine metabolism-related enzyme genes into plants results in plants with significantly improved herbicidal stress resistance.

What is claimed is:

1. A method for producing transgenic plants with improved environmental stress tolerance against at least one environmental stress selected from drought stress, cold stress, salt stress, osmotic stress, or herbicidal stress as compared to wild type plants of the same species, the method comprising (1) integrating into the genome of the plant a vector comprising a DNA molecule encoding an exogenous spermidine synthase wherein the DNA molecule encoding spermidine synthase comprises SEQ ID NO: 1 or a nucleotide sequence encoding the amino acid sequence of SEQ ID NO: 2 and (2) growing said plant, wherein said DNA molecule is expressed and wherein said spermidine synthase confers on said transgenic plant an improved tolerance to said environmental stress.

2. The method of claim 1, wherein the plant is a dicotyledon.

3. A method for producing transgenic plants with improved growth in conditions of environmental stress, the method comprising (1) integrating into the genome of the plant a vector comprising a DNA molecule encoding an exogenous spermidine synthase, and wherein the DNA molecule comprises SEQ ID NO: 1 or a nucleotide sequence encoding the amino acid sequence of SEQ ID NO: 2; or (ii) a base sequence encoding for the amino acid sequence of SEQ ID NO: 2; and (2) growing said plant in conditions of environmental stress selected from drought stress, cold stress, salt stress, osmotic stress, or herbicidal stress, wherein said DNA molecule is expressed and wherein said spermidine synthase confers on said transgenic plant improved growth than wild type plants of the same species in conditions of said environmental stress.

4. A transgenic plant and its progeny produced from the method of claim 1 or 3, wherein said progeny comprises said DNA molecule.

5. Leaves, stems, flowers, ovaries, fruit, seeds, fibers or callus obtained from the plant or progeny of the plant of claim 4, wherein said leaves, stems, flowers, ovaries, fruit, seeds, fibers or callus comprise said DNA molecule.

6. The plant of claim 4, wherein the plant is *Arabidopsis thaliana*.

7. The plant of claim 4, wherein the plant is a dicotyledon.

8. An isolated *Cucurbita ficifolia* Bouche spermidine synthase (SPDS) encoded by a nucleic acid comprising base number 77 through 1060 of SEQ ID NO: 1.

9. An isolated spermidine synthase nucleic acid comprising base number 77 through 1060 of SEQ ID NO:1.

10. A plasmid comprising the isolated spermidine synthase nucleic acid of claim 9.

11. A transformed plant comprising the plasmid according to claim 10.

* * * * *